US009114390B2

(12) United States Patent
Iwabuchi et al.

(10) Patent No.: US 9,114,390 B2
(45) Date of Patent: Aug. 25, 2015

(54) 9-AZANORADAMANTANE N—OXYL COMPOUND AND METHOD FOR PRODUCING SAME, AND ORGANIC OXIDATION CATALYST AND METHOD FOR OXIDIZING ALCOHOLS USING 9-AZANORADAMANTANE N—OXYL COMPOUND

(71) Applicant: TOHOKU UNIVERSITY, Miyagi (JP)

(72) Inventors: Yoshiharu Iwabuchi, Miyagi (JP); Masatoshi Shibuya, Miyagi (JP); Ryusuke Doi, Miyagi (JP)

(73) Assignee: TOHOKU UNIVERSITY (JP)

( * ) Notice: Subject to any disclaimer, the term of this patent is extended or adjusted under 35 U.S.C. 154(b) by 0 days.

(21) Appl. No.: 14/380,794

(22) PCT Filed: Feb. 22, 2013

(86) PCT No.: PCT/JP2013/054554
§ 371 (c)(1),
(2) Date: Aug. 25, 2014

(87) PCT Pub. No.: WO2013/125688
PCT Pub. Date: Aug. 29, 2013

(65) Prior Publication Data

US 2015/0031887 A1 Jan. 29, 2015

(30) Foreign Application Priority Data

Feb. 24, 2012 (JP) ................................ 2012-039362

(51) Int. Cl.

| | |
|---|---|
| ***C07D 221/22*** | (2006.01) |
| ***C07C 45/29*** | (2006.01) |
| ***C07D 451/14*** | (2006.01) |
| ***B01J 31/02*** | (2006.01) |
| ***B01J 31/00*** | (2006.01) |
| ***C07C 67/313*** | (2006.01) |
| ***C07B 63/04*** | (2006.01) |

(52) U.S. Cl.
CPC ............ *B01J 31/0271* (2013.01); *B01J 31/006* (2013.01); *C07B 63/04* (2013.01); *C07C 45/29* (2013.01); *C07C 67/313* (2013.01); *C07D 221/22* (2013.01); *C07D 451/14* (2013.01); *B01J 2231/70* (2013.01); *C07C 2101/16* (2013.01); *C07C 2103/52* (2013.01); *C07C 2527/24* (2013.01)

(58) Field of Classification Search
CPC ..... C07D 221/22; C07D 451/14; C07C 45/29
USPC ........................................................... 546/72
See application file for complete search history.

(56) References Cited

U.S. PATENT DOCUMENTS

| | | | | |
|---|---|---|---|---|
| 7,705,152 B2 | 4/2010 | Iwabuchi et al. | ............. | 546/137 |
| 2007/0232838 A1 | 10/2007 | Iwabuchi et al. | ............. | 568/700 |
| 2009/0124806 A1 | 5/2009 | Iwabuchi et al. | ............... | 546/72 |
| 2013/0172543 A1 | 7/2013 | Iwabuchi et al. | ............ | 536/27.6 |

FOREIGN PATENT DOCUMENTS

| | | | | |
|---|---|---|---|---|
| JP | 2008212853 | | 9/2008 | ............... B01J 31/02 |
| JP | 2009114143 | | 5/2009 | ........... C07C 201/12 |
| WO | WO2006001387 | | 1/2006 | ............... B01J 31/02 |
| WO | WO2009145323 | | 12/2009 | ............. C07C 45/38 |
| WO | 2012008228 | * | 1/2012 | |
| WO | WO2012008228 | | 1/2012 | ............. C07C 45/30 |

OTHER PUBLICATIONS

Capiomont et al., Acta crystallographica, section B: structural crystallography and crystal chemistry (1977), B33 (10), 3040-4.*
International Preliminary Report on Patentability issued in corresponding application PCT/JP2013/054554, dated Sep. 4, 2014 (5 pgs).
International Search Report issued in corresponding application No. PCT/JP2013/054554, dated Mar. 26, 2013 (2 pgs).
Anelli et al., "Fast and Selective Oxidation of Primary Alcohols to Aldehydes or to Carboxylic Acids and of Secondary Alcohols to Ketones Mediated by Oxoammonium Salts under Two-Phase Conditions," The Journal of Organic Chemistry, vol. 52, Issue 12, pp. 2559-2562, 1987.
De Mico et al., "A Versatile and Highly Selective Hypervalent Iodine (III)/2,2,6,6-Tetramethyl-1-piperidinyloxyl-Mediated Oxidation of Alcohols to Carbonyl Compounds," The Journal of Organic Chemistry, vol. 62, Issue 20, pp. 6974-6977, 1997.
Liu et al., "Transition-Metal-Free: A Highly Efficient Catalytic Aerobic Alcohol Oxidation Process," Journal of the American Chemical Society, vol. 126, Issue 13, pp. 4112-4113, 2004.
Shibuya et al., "2-Azaadamantane *N*—Oxyl (AZADO) and 1-Me-AZADO: Highly Efficient Organocatalysts for Oxidation of Alcohols," Journal of the American Chemical Society, vol. 128, Issue 26, pp. 8412-8413, 2006.
Shibuya et al., "Oxoammonium salt/$NaClO_2$: an expedient, catalytic system for one-pot oxidation of primary alcohols to carboxylic acids with broad substrate applicability," Chemical Communications, Issue 13, pp. 1739- 1741, 2009.

(Continued)

*Primary Examiner* — Niloofar Rahmani
(74) *Attorney, Agent, or Firm* — Hayes Soloway P.C.

(57) ABSTRACT

An organocatalyst for oxidizing alcohols in which a primary alcohol is selectively oxidized in a polyol substrate having a plurality of alcohols under environmentally-friendly conditions. The organic oxidation catalyst has an oxygen atom bonded to a nitrogen atom of an azanoradamantane skeleton and at least one alkyl group at positions 1 and 5. The oxidation catalyst has higher activity than TEMPO, which is an existing oxidation catalyst, in the selective oxidation reaction of primary alcohols, and better selectivity than AZADO and 1-Me-AZADO. This DMN-AZADO can be applied to the selective oxidation reaction of primary alcohols that contributes to shortening the synthesizing process for pharmaceuticals, pharmaceutical raw materials, agricultural chemicals, cosmetics, organic materials, and other such high value-added organic compounds.

16 Claims, No Drawings

(56) References Cited

OTHER PUBLICATIONS

Shibuya et al., "An Expeditious Entry to 9-Azabicyclo[3.3.1]nonane *N*—Oxyl (ABNO): Another Highly Active Organocatalyst for Oxidation of Alcohols," The Journal of Organic Chemistry, vol. 74, Issue 12, pp. 4619-4622, 2009.

Shibuya et al., "Practical Preparation Methods for Highly Active Azaadamantane-Nitroxyl-Radical-Type Oxidation Catalysts," Synthesis, Issue 21, pp. 3418-3425, 2011.

Hayashi et al., "9-Azanoradamantane *N*-Oxyl (Nor-AZADO): A Highly Active Organocatalyst for Alcohol Oxidation," Chemical and Pharmaceutical Bulletin, vol. 59, Issue 12, pp. 1570-1573, 2011.

Siedlecka et al., "Selective Oxidation of Primary Hydroxy Groups in Primary-Secondary Diols", Tetrahedron Letters, vol. 31, Issue 15, pp. 2177-2180, 1990.

Greene et al., "Protective Groups in Organic Synthesis," 3rd Edition, 1999, John Wiley & Sons, Inc. (8 pgs).

* cited by examiner

9-AZANORADAMANTANE N—OXYL COMPOUND AND METHOD FOR PRODUCING SAME, AND ORGANIC OXIDATION CATALYST AND METHOD FOR OXIDIZING ALCOHOLS USING 9-AZANORADAMANTANE N—OXYL COMPOUND

TECHNICAL FIELD

The present invention relates to 9-azanoradamantane N-oxyl compounds, organic oxidation catalysts containing 9-azanoradamantane N-oxyl compounds, methods for producing 9-azanoradamantane N-oxyl compounds, and alcohol oxidation methods for selectively oxidizing primary alcohol with the 9-azanoradamantane N-oxyl compounds.

BACKGROUND ART

Oxidation reactions of alcohols to carbonyl compounds represent one of the most fundamental reactions used for the organic syntheses of high value-added compounds such as medicaments, agricultural chemicals, flavoring ingredients, and chemical products. For this reason, many techniques have been developed in the past years. However, many of these methods involve use of toxic and explosive oxidizing agents, or require extremely low temperatures of −40 degrees or less. Over these backgrounds, a technique that uses 2,2,6,6-tetramethylpiperidine 1-oxyl (hereinafter also referred to as "TEMPO") has attracted interest as a method that permits large-scale oxidation by taking advantage of the ability of this catalyst to oxidize alcohol even under very mild conditions of from 0 degree to room temperature using various co-oxidizing agents without using high toxicity reagents. It has been reported that many oxidizing agents have potential use as co-oxidizing agents (Non Patent Literature 3), including, for example, a low-cost and environmentally friendly sodium hypochlorite aqueous solution used in industrial and other processes (Non Patent Literature 1), iodobenzenediacetate ($PhI(OAc)_2$) that can coexist with a wide range of functional groups even in applications that use alcohols having double bonds and electron-rich aromatic rings (Non Patent Literature 2), and a molecular oxygen having high safety and high atom efficiency. The present inventors have reported that a nitroxyl radical having an azaadamantane skeleton (2-azaadamantane N-oxyl (hereinafter, also referred to as "AZADO"), and 1-methyl-2-azaadamantane N-oxyl (hereinafter, also referred to as "1-Me-AZADO")), a nitroxyl radical having an azabicyclo[3.3.1]nonane skeleton (9-azabicyclo[3.3.1]nonane N-oxyl), and 9-azanoradamantane N-oxyl having an azanoradamantane skeleton (hereinafter, also referred to as "Nor-AZADO") have higher catalytic activity than TEMPO, and promote a fast oxidation of bulky secondary alcohols that cannot be oxidized with TEMPO (Non Patent Literatures 4, 5, 6, 7, 8, and Patent Literatures 1, 2, 3, 4, and 5).

In oxidation reactions catalyzed by TEMPO, reaction that selectively oxidizes primary alcohols proceeds with a substrate that includes both primary alcohol and secondary alcohol (Non Patent Literature 9). Such selective oxidation of a specific alcohol is important as an alternative method of distinguishing a functional group in the synthesis of polyfunctional compounds commonly distinguished and synthesized with a protecting group. Such a reaction is also important because it can contribute to simplifying the synthesis process with the single step of alcohol oxidation reaction, as opposed to using a protecting group that requires protecting and deprotecting steps. In fact, there are many reports of synthesizing natural products using such reactions.

CITATION LIST

Patent Literature

Patent Document 1: WO2006/001387

Patent Document 2: JP-A-2009-114143

Patent Document 3: JP-A-2008-212853

Patent Document 4: WO2009/145323

Patent Document 5: WO2012/008228

Non Patent Literature

Non Patent Document 1: The Journal of Organic Chemistry, Vol. 52, Issue 12, pp. 2559-2562, 1987

Non Patent Document 2: The Journal of Organic Chemistry, Vol. 62, Issue 20, pp. 6974-6977, 1997

Non Patent Document 3: Journal of the American Chemical Society, Vol. 126, Issue 13, pp. 4112-4113, 2004

Non Patent Document 4: Journal of the American Chemical Society, Vol. 128, Issue 26, pp. 8412-8413, 2006

Non Patent Document 5: Chemical Communications, Issue 13, pp 1739-1741, 2009

Non Patent Document 6: The Journal of Organic Chemistry, Vol. 74, Issue 12, pp. 4619-4622, 2009

Non Patent Document 7: Syntheses, Issue 21, pp 3418-3425, 2011

Non Patent Document 8: Chemical and Pharmaceutical Bulletin, Vol. 59, Issue 12, pp 1570-1573, 2011

Non Patent Document 9: Tetrahedron Letters, Vol. 31, Issue 15, pp. 2177-2180, 1990

SUMMARY OF INVENTION

Technical Problem

However, the reactivity of TEMPO oxidation is not sufficient, and the reaction often requires large catalytic amounts of 20 mol % or higher, and a long reaction time. This may lead to poor yield. Further, TEMPO oxidation is not always applicable, and may necessitate changing the synthesis route.

The present inventors conducted intensive studies of catalysts that have higher activity than TEMPO yet maintain selectivity for primary alcohols, and found that 9-azanoradamantane N-oxyl compounds having an azanoradamantane skeleton with at least one alkyl group substituted at positions 1 and 5, and an oxygenated nitrogen atom show high catalytic activity for alcohol oxidation. The present invention was completed on the basis of this finding.

Solution to Problem

Specifically, the present invention is concerned with 9-azanoradamantane N-oxyl compounds, methods for producing same, and organic oxidation catalysts and alcohol oxidation methods that use the 9-azanoradamantane N-oxyl compounds.

(1) A 9-azanoradamantane N-oxyl compound represented by the following formula (1).

{Chem. 1}

(1)

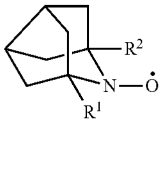

(In the formula (1), $R^1$ and $R^2$ represent hydrogen atoms or alkyl groups. When one of $R^1$ and $R^2$ is hydrogen, the other is an alkyl group.)

(2) An organic oxidation catalyst that comprises the 9-azanoradamantane N-oxyl compound of (1).

(3) The catalyst of (2), wherein the catalyst has primary alcohol selectivity.

(4) A method for producing the 9-azanoradamantane N-oxyl compound represented by the formula (1), the method producing the 9-azanoradamantane N-oxyl compound through at least a step of oxidizing an azanoradamantane compound represented by the following formula (2).

{Chem. 2}

(2)

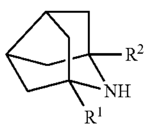

(In the formula (2), $R^1$ and $R^2$ have the same definitions as described above.)

(5) A method for producing the 9-azanoradamantane N-oxyl compound represented by the formula (1), the method producing the 9-azanoradamantane N-oxyl compound through at least a step of closing the ring of a hydrazonoazabicyclo[3.3.1]nonane compound of the formula (3) below and forming an azanoradamantane ring, and oxidizing the resulting azanoradamantane compound represented by the formula (2).

{Chem. 3}

(3)

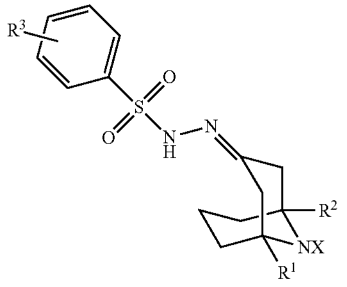

(In the formula (3), $R^1$ and $R^2$ have the same definitions as described above; $R^3$ represents at least one substituent selected from the group consisting of a hydrogen atom, a halogen atom, a nitro group, a cyano group, a hydroxyl group, a mercapto group, an amino group, a formyl group, a carboxyl group, a sulfo group, a linear or branched $C_{1-12}$ alkyl group, a $C_{3-12}$ cycloalkyl group, a ($C_{1-12}$ alkyl)oxy group, a ($C_{3-12}$ cycloalkyl)oxy group, a ($C_{1-12}$ alkyl)thio group, a ($C_{3-12}$ cycloalkyl)thio group, a ($C_{1-12}$ alkyl)amino group, a ($C_{3-12}$ cycloalkyl)amino group, a di($C_{1-6}$ alkyl)amino group, a di($C_{3-6}$ cycloalkyl)amino group, a $C_{1-12}$ alkylcarbonyl group, a $C_{3-12}$ cycloalkylcarbonyl group, a ($C_{1-12}$ alkyl)oxycarbonyl group, a ($C_{3-12}$ cycloalkyl)oxycarbonyl group, a ($C_{1-12}$ alkyl) thiocarbonyl group, a ($C_{3-12}$ cycloalkyl)thiocarbonyl group, a ($C_{1-12}$ alkyl)aminocarbonyl group, a ($C_{3-12}$ cycloalkyl)aminocarbonyl group, a di($C_{1-6}$ alkyl)aminocarbonyl group, a di($C_{3-6}$ cycloalkyl)aminocarbonyl group, a ($C_{1-22}$ alkyl)carbonyloxy group, a ($C_{3-12}$ cycloalkyl)carbonyloxy group, a ($C_{1-12}$ alkyl)carbonylthio group, a ($C_{3-12}$ cycloalkyl)carbonylthio group, a ($C_{1-12}$ alkyl)carbonylamino group, a ($C_{3-12}$ cycloalkyl)carbonylamino group, a di($C_{1-12}$ alkylcarbonyl) amino group, a di($C_{3-12}$ cycloalkylcarbonyl)amino group, a $C_{1-6}$ haloalkyl group, a $C_{3-6}$ halocycloalkyl group, a $C_{2-6}$ alkenyl group, a $C_{3-6}$ cycloalkenyl group, a $C_{2-6}$ haloalkenyl group, a $C_{3-6}$ halocycloalkenyl group, a $C_{2-6}$ alkynyl group, a $C_{2-6}$ haloalkynyl group, a benzyl group which may be optionally substituted with Ra, a benzyloxy group which may be optionally substituted with Ra, a benzylthio group which may be optionally substituted with Ra, a benzylamino group which may be optionally substituted with Ra, a dibenzylamino group which may be optionally substituted with Ra, a benzylcarbonyl group which may be optionally substituted with Ra, a benzyloxycarbonyl group which may be optionally substituted with Ra, a benzylthiocarbonyl group which may be optionally substituted with Ra, a benzylaminocarbonyl group which may be optionally substituted with Ra, a dibenzylaminocarbonyl group which may be optionally substituted with Ra, a benzylcarbonyloxy group which may be optionally substituted with Ra, a benzylcarbonylthio group which may be optionally substituted with Ra, a benzylcarbonylamino group which may be optionally substituted with Ra, a di(benzylcarbonyl)amino group which may be optionally substituted with Ra, an aryl group which may be optionally substituted with Ra, an aryloxy group which may be optionally substituted with Ra, an arylthio group which may be optionally substituted with Ra, an arylamino group which may be optionally substituted with Ra, a diarylamino group which may be optionally substituted with Ra, an arylcarbonyl group which may be optionally substituted with Ra, an aryloxycarbonyl group which may be optionally substituted with Ra, an arylthiocarbonyl group which may be optionally substituted with Ra, an arylaminocarbonyl group which may be optionally substituted with Ra, a diarylaminocarbonyl group which may be optionally substituted with Ra, an arylcarbonyloxy group which may be optionally substituted with Ra, an arylcarbonylthio group which may be optionally substituted with Ra, an arylcarbonylamino group which may be optionally substituted with Ra, and a di(arylcarbonyl)amino group which may be optionally substituted with Ra, wherein the substituents may be the same or different when two or more substituents exist; Ra represents halogen, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkyl sulfenyl $C_{1-6}$ alkyl group, a $C_{1-6}$ haloalkoxy group, $C_{1-6}$ alkyl sulfenyl group, a $C_{1-6}$ alkylsulfinyl group, a $C_{1-6}$ alkylsulfonyl group, a $C_{1-6}$ haloalkylsulfenyl group, a $C_{1-6}$ haloalkylsulfinyl group, a $C_{1-6}$ haloalkylsulfonyl group, a $C_{2-6}$ alkenyl group, a $C_{2-6}$ haloalkenyl group, a $C_{2-6}$ alkenyloxy group, a $C_{2-6}$ haloalkenyloxy group, a $C_{2-6}$ alkenylsulfenyl group, a $C_{2-6}$ alkenylsulfinyl group, a $C_{2-6}$ alkenylsulfonyl group, a $C_{2-6}$ haloalkenylsulfenyl group, a $C_{2-6}$ haloalkenylsulfinyl group, a $C_{2-6}$ haloalkenylsulfonyl group, a $C_{2-6}$ alkynyl group, a $C_{2-6}$ haloalkynyl group, a $C_{2-6}$ alkynyloxy group, a $C_{2-6}$ haloalkynyloxy group, a $C_{2-6}$ alkynyl sulfenyl group, a $C_{2-6}$ alkynylsulfinyl group, a $C_{2-6}$ alkynylsulfonyl group, a $C_{2-6}$ haloalkynyl sulfenyl group, a $C_{2-6}$ haloalkynylsulfinyl group, a $C_{2-6}$ haloalkynylsulfonyl group, —$NO_2$, —CN, a formyl group, —OH, —SH, —$NH_2$, —SCN, a $C_{1-6}$ alkoxycarbonyl group, a $C_{1-6}$ alkylcarbonyl group, a $C_{1-6}$ haloalkylcarbonyl group, a $C_{1-6}$ alkylcarbonyloxy group, a phenyl group, a $C_{1-6}$ alkylamino group, or a di $C_{1-6}$ alkylamino group, wherein Ra is substituted in numbers of 1 to 5, and may be the same or different when two or more Ra exist; and X represents a hydrogen atom, or a group selected from an acyl group, a carbamoyl group, a sulfoneamide group, an alkyl group, an allyl group, a benzyl group, an aryl group, a silyl group, a hydroxyl group, an alkoxy group, and an oxygen atom.)

(6) A method for producing the 9-azanoradamantane N-oxyl compound represented by the formula (1), the method producing the 9-azanoradamantane N-oxyl compound through at least a step of condensing a keto-azabicyclo[3.3.1]nonane compound of the formula (4) below with phenylhydrazine, closing the ring of the resulting hydrazonoazabicyclo[3.3.1]nonane of the formula (3) and forming an azanoradamantane ring, and oxidizing the resulting azanoradamantane compound represented by the formula (2).

{Chem. 4}

(4)

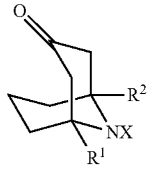

(In the formula (4), $R^1$, $R^2$, and X have the same definitions as described above.)

(7) A method for producing the azanoradamantane N-oxyl compound represented by the formula (1), the method comprising:

synthesizing a ketobicycloamine product through condensation of 2,6-heptanedione, ammonium chloride, and acetonedicarboxylic acid, the 2,6-heptanedione being obtained by methylating a Weinreb diamide produced from glutaryl chloride;

producing a hydrazone through condensation of the ketobicycloamine product with hydrazine;

forming an azanoradamantane skeleton under basic condition; and oxidizing the amino group.

(8) A method for oxidizing alcohols, the method comprising oxidizing an alcohol in the presence of the 9-azanoradamantane N-oxyl compound of (1) to synthesize a corresponding oxo product.

(9) The method according to (8), wherein the oxidation is performed in the presence of a co-oxidizing agent.

(10) The method according to (8), wherein the alcohol is a compound that includes a primary alcohol and/or a secondary alcohol.

(11) The method according to (8), wherein the alcohol is a compound that includes a primary alcohol and a secondary alcohol, and wherein the method selectively oxidizes the primary alcohol.

(12) The method according to any one of (8) to (11), wherein the 9-azanoradamantane N-oxyl compound is added in 0.001 mol % to 1000 mol % with respect to the alcohol.

(13) The method according to any one of (9) to (12), wherein the co-oxidizing agent is an oxidizing agent selected from the group consisting of peroxy acid, hydrogen peroxide, hypohalous acid and salts thereof, perhalic acid and salts thereof, persulfates, halides, halogenating agents, trihaloisocyanuric acids, (diacetoxyiodo)arenes, oxygen, and air.

Advantageous Effects of Invention

A nitroxyl radical having an azanoradamantane skeleton with at least one alkyl group substituted at positions 1 and 5 is used as an oxidation catalyst to enable a more efficient primary alcohol selective oxidation reaction that requires less catalytic amounts and a shorter reaction time than a reaction catalyzed by the conventional TEMPO with a substrate that includes both primary alcohol and secondary alcohol. Primary alcohols can be oxidized with higher selectivity than that of AZADO and 1-Me-AZADO.

DESCRIPTION OF EMBODIMENTS

The following specifically describes the 9-azanoradamantane N-oxyl compounds of the present invention, methods for producing same, and organic oxidation catalysts and alcohol oxidation methods that use the 9-azanoradamantane N-oxyl compounds.

As used herein, "primary alcohol selective oxidation", "primary alcohol selective oxidation reaction", "primary alcohol selective oxidation catalyst", "primary alcohol selectivity", and other such language used in the same meaning mean reactions, functions, and catalysts with which 50% or more, preferably 70% or more, further preferably 90% or more of the reaction product of an oxidation reaction of a substrate that includes both primary alcohol and secondary alcohol are the oxidation product of solely the primary alcohol.

The present invention uses the 9-azanoradamantane N-oxyl compound of the following formula (1) as an organic oxidation catalyst.

{Chem. 5}

(1)

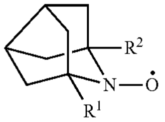

(In the formula (1), $R^1$ and $R^2$ represent hydrogen atoms or alkyl groups. When one of $R^1$ and $R^2$ is hydrogen, the other is an alkyl group.)

The alkyl groups represented by $R^1$ and $R^2$ of the formula (1) are not particularly limited, as long as these are known in the art, and can achieve the intended object. Examples include lower alkyl groups. Examples of the lower alkyl groups include $C_{1-5}$ alkyl groups, specifically, methyl, ethyl, propyl, isopropyl, n-butyl, i-butyl, sec-butyl, t-butyl, and pentyl. Particularly preferred is methyl.

The compound represented by the foregoing formula (1) may be synthesized through at least a step of oxidizing an azanoradamantane compound represented by the following formula (2).

{Chem. 6}

(2)

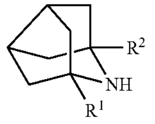

(In the formula (2), $R^1$ and $R^2$ have the same definitions as described above.)

The azanoradamantane compound represented by the foregoing formula (2) may be synthesized by closing the ring of a hydrazonoazabicyclo[3.3.1]nonane compound of the following formula (3) and forming an azanoradamantane ring.

{Chem. 7}

(3)

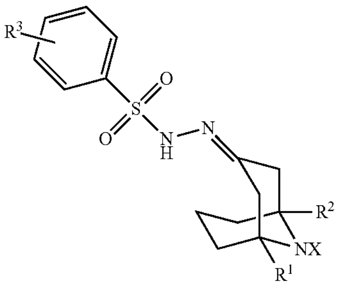

(In the formula (3), $R^1$ and $R^2$ have the same definitions as described above; $R^3$ represents at least one substituent selected from the group consisting of a hydrogen atom, a halogen atom, a nitro group, a cyano group, a hydroxyl group, a mercapto group, an amino group, a formyl group, a carboxyl group, a sulfo group, a linear or branched $C_{1-12}$ alkyl group, a $C_{3-12}$ cycloalkyl group, a ($C_{1-12}$ alkyl)oxy group, a ($C_{3-12}$ cycloalkyl)oxy group, a ($C_{1-12}$ alkyl)thio group, a ($C_{3-12}$ cycloalkyl)thio group, a ($C_{1-12}$ alkyl)amino group, a ($C_{3-12}$ cycloalkyl)amino group, a di($C_{1-6}$ alkyl)amino group, a di($C_{3-6}$ cycloalkyl)amino group, a $C_{1-12}$ alkylcarbonyl group, a $C_{3-12}$ cycloalkylcarbonyl group, a ($C_{1-12}$ alkyl)oxycarbonyl group, a ($C_{3-12}$ cycloalkyl)oxycarbonyl group, a ($C_{1-12}$ alkyl) thiocarbonyl group, a ($C_{3-12}$ cycloalkyl)thiocarbonyl group, a ($C_{1-12}$ alkyl)aminocarbonyl group, a ($C_{3-12}$ cycloalkyl)aminocarbonyl group, a di($C_{1-6}$ alkyl)aminocarbonyl group, a di($C_{3-6}$ cycloalkyl)aminocarbonyl group, a ($C_{1-12}$ alkyl)carbonyloxy group, a ($C_{3-12}$ cycloalkyl)carbonyloxy group, a ($C_{1-12}$ alkyl)carbonylthio group, a ($C_{3-12}$ cycloalkyl)carbonylthio group, a ($C_{1-12}$ alkyl)carbonylamino group, a ($C_{3-12}$ cycloalkyl)carbonylamino group, a di($C_{1-12}$ alkylcarbonyl) amino group, a di($C_{3-12}$ cycloalkylcarbonyl)amino group, a $C_{1-6}$ haloalkyl group, a $C_{3-6}$ halocycloalkyl group, a $C_{2-6}$ alkenyl group, a $C_{3-6}$ cycloalkenyl group, a $C_{2-6}$ haloalkenyl group, a $C_{3-6}$ halocycloalkenyl group, a $C_{2-6}$ alkynyl group, a $C_{2-6}$ haloalkynyl group, a benzyl group which may be optionally substituted with Ra, a benzyloxy group which may be optionally substituted with Ra, a benzylthio group which may be optionally substituted with Ra, a benzylamino group which may be optionally substituted with Ra, a dibenzylamino group which may be optionally substituted with Ra, a benzylcarbonyl group which may be optionally substituted with Ra, a benzyloxycarbonyl group which may be optionally substituted with Ra, a benzylthiocarbonyl group which may be optionally substituted with Ra, a benzylaminocarbonyl group which may be optionally substituted with Ra, a dibenzylaminocarbonyl group which may be optionally substituted with Ra, a benzylcarbonyloxy group which may be optionally substituted with Ra, a benzylcarbonylthio group which may be optionally substituted with Ra, a benzylcarbonylamino group which may be optionally substituted with Ra, a di(benzylcarbonyl)amino group which may be optionally substituted with Ra, an aryl group which may be optionally substituted with Ra, an aryloxy group which may be optionally substituted with Ra, an arylthio group which may be optionally substituted with Ra, an arylamino group which may be optionally substituted with Ra, a diarylamino group which may be optionally substituted with Ra, an arylcarbonyl group which may be optionally substituted with Ra, an aryloxycarbonyl group which may be optionally substituted with Ra, an arylthiocarbonyl group which may be optionally substituted with Ra, an arylaminocarbonyl group which may be optionally substituted with Ra, a diarylaminocarbonyl group which may be optionally substituted with Ra, an arylcarbonyloxy group which may be optionally substituted with Ra, an arylcarbonylthio group which may be optionally substituted with Ra, an arylcarbonylamino group which may be optionally substituted with Ra, and a di(arylcarbonyl)amino group which may be optionally substituted with Ra, wherein the substituents may be the same or different when two or more substituents exist; Ra represents halogen, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkyl sulfenyl $C_{1-6}$ alkyl group, a $C_{1-6}$ haloalkoxy group, a $C_{1-6}$ alkyl sulfenyl group, a $C_{1-6}$ alkylsulfinyl group, a $C_{1-6}$ alkylsulfonyl group, a $C_{1-6}$ haloalkylsulfenyl group, a $C_{1-6}$ haloalkylsulfinyl group, a $C_{1-6}$ haloalkylsulfonyl group, a $C_{2-6}$ alkenyl group, a $C_{2-6}$ haloalkenyl group, a $C_{2-6}$ alkenyloxy group, a $C_{2-6}$ haloalkenyloxy group, a $C_{2-6}$ alkenylsulfenyl group, a $C_{2-6}$ alkenylsulfinyl group, a $C_{2-6}$ alkenylsulfonyl group, a $C_{2-6}$ haloalkenylsulfenyl group, a $C_{2-6}$ haloalkenylsulfinyl group, a $C_{2-6}$ haloalkenylsulfonyl group, a $C_{2-6}$ alkynyl group, a $C_{2-6}$ haloalkynyl group, a $C_{2-6}$ alkynyloxy group, a $C_{2-6}$ haloalkynyloxy group, a $C_{2-6}$ alkynyl sulfenyl group, a $C_{2-6}$ alkynylsulfinyl group, a $C_{2-6}$ alkynylsulfonyl group, a $C_{2-6}$ haloalkynyl sulfenyl group, a $C_{2-6}$ haloalkynylsulfinyl group, a $C_{2-6}$ haloalkynylsulfonyl group, $—NO_2$, —CN, a formyl group, —OH, —SH, $—NH_2$, —SCN, a $C_{1-6}$ alkoxycarbonyl group, a $C_{1-6}$ alkylcarbonyl group, a $C_{1-6}$ haloalkylcarbonyl group, a $C_{1-6}$ alkylcarbonyloxy group, a phenyl group, a $C_{1-6}$ alkylamino group, or a di $C_{1-6}$ alkylamino group, wherein Ra is substituted in numbers of 1 to 5, and may be the same or different when two or more Ra exist; and X represents a hydrogen atom, or a group selected from an acyl group, a carbamoyl group, a sulfoneamide group, an alkyl group, an allyl group, a benzyl group, an aryl group, a silyl group, a hydroxyl group, an alkoxy group, and an oxygen atom.)

X may be groups other than those exemplified above, provided that such groups do not have an adverse effect on the reaction that closes the ring of the hydrazono[3.3.1]nonane compound and forms the azanoradamantane ring.

Examples of the acyl group representing X include $C_{1-10}$ acyl groups such as formyl, acetyl, propanoyl, pivaloyl, and benzoyl. Examples of the carbamoyl group include $C_{1-10}$ carbamoyl groups such as methoxycarbonyl, ethoxycarbonyl, tert-butoxycarbonyl, and benzyloxycarbonyl. Examples of the sulfoneamide group include sulfoneamide groups such as methanesulfoneamide, trifluoromethanesulfoneamide, ethanesulfoneamide, toluenesulfoneamide, and nitrotoluenesulfoneamide. Examples of the aryl group include $C_{6-18}$ aryl groups such as phenyl, tolyl, and xylyl. Examples of the silyl group include silyl groups with substituted three alkyl groups, such as trimethylsilyl, triethylsilyl, triisopropylsilyl, and tert-butyldimethylsilyl. Examples of the alkoxy group include $C_{1-10}$ alkoxy groups such as methoxy, ethoxy, and propoxy. The alkyl groups are as described for $R^1$.

The compound represented by the foregoing formula (3) may be synthesized by condensation of a keto-azabicyclo [3.3.1]nonane compound represented by the following formula (4) with phenylhydrazine.

{Chem. 8}

(4)

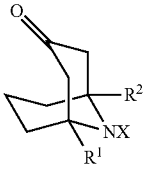

(In the formula (4), $R^1$, $R^2$, and X have the same definitions as described above.)

The compound represented by the foregoing formula (4) may be synthesized by condensing 2,6-heptanedione, ammonium chloride, and acetonedicarboxylic acid, the 2,6-heptanedione being obtained by methylating a Weinreb diamide produced from glutaryl chloride.

Evidently, the synthesis methods above are merely examples of methods used to synthesize the compound represented by the formula (1), and different methods may be used. The compounds represented by the formulae (1) to (4) include derivatives in which the azanoradamantane core is substituted with substituents such as an alkyl group, a halogen atom, and an alkoxy group at positions other than positions 1 and 5.

The alcohols to be oxidized in the present invention may be primary alcohols represented by the following general formula (5), or secondary alcohols represented by the following general formula (6).

{Chem. 9}

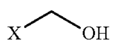

(5)

{Chem. 10}

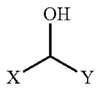

(6)

The substituents X and Y in the general formulae (5) and (6) are not particularly limited, as long as these are substituents that do not have an adverse effect on the oxidation reaction. For example, X and Y may be optionally substituted linear or branched alkyl groups, optionally substituted cyclic alkyl groups, optionally substituted aromatic hydrocarbon groups, or optionally substituted aromatic heterocyclic groups. Other examples include compounds that have more than one of the structure units of the general formulae (5) and (6) within the molecule.

Examples of the linear or branched alkyl group of the optionally substituted linear or branched alkyl groups represented by X and Y include alkyl groups of about 1 to 16 carbon atoms, preferably alkyl groups of about 1 to 8 carbon atoms. Examples of such alkyl groups include methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, and 5,5-dimethylhexyl.

The cyclic alkyl group may be, for example, cycloalkyl of about 3 to 7 carbon atoms, for example, such as cyclopropyl, cyclobutyl, cyclopentyl, cyclohexyl, and cycloheptyl.

The aromatic ring forming the aromatic cyclic hydrocarbon group may be a monocyclic aromatic hydrocarbon ring or a fused polycyclic aromatic hydrocarbon ring. Examples of the aromatic hydrocarbon group include aryl groups of about 6 to 14 carbon atoms, such as phenyl, naphthyl, anthryl, azulenyl, phenanthryl, and acenaphthylenyl.

Non-limiting examples of the heterocyclic ring forming the aromatic heterocyclic group include a five-membered or six-membered monocyclic heterocyclic ring, and a six-membered+five-membered, or six-membered+six-membered fused heterocyclic ring. The ring-forming heteroatom of the heterocyclic ring may be, but is not limited to, for example, 1 to 3 atoms selected from an oxygen atom, a sulfur atom, and a nitrogen atom. The heterocyclic ring is preferably an aromatic ring, and may be saturated or partially saturated. When the heterocyclic ring is saturated or partially saturated, the heteroatom moiety is preferably protected by a suitable protecting group, or may not be protected at all.

Examples of the aromatic heterocyclic group include monocyclic aromatic heterocyclic groups such as furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, and triazinyl; and 8- to 12-membered fused polycyclic aromatic heterocyclic groups such as benzofuranyl, isobenzofuranyl, benzo[b]thienyl, indolyl, isoindolyl, 1H-indazolyl, benzindazolyl, benzooxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-b]pyridazinyl. These aromatic heterocyclic groups may be saturated or partially saturated.

As used herein, "a group being optionally substituted" means that one or more of any substituents may exist at any position of the group, and the substituents may be the same or different when two or more substituents exist. The substituent is not particularly limited, as long as it is not detrimental to the reaction.

Examples of the substituents that may be present on the linear or branched alkyl group, the cyclic alkyl group, the aromatic hydrocarbon group, or the aromatic heterocyclic group include, but are not limited to, alkyl groups of about 1 to 6 carbon atoms (such as methyl, ethyl, and propyl), alkoxy groups of about 1 to 6 carbon atoms (such as methoxy, ethoxy, and propoxy), halogen atoms (such as a fluorine atom, a chlorine atom, a bromine atom, and an iodine atom), alkenyl groups of about 2 to 6 carbon atoms (such as vinyl, and allyl), alkynyl groups of about 2 to 6 carbon atoms (such as ethynyl, and propargyl), hydroxyl groups, optionally substituted amino groups, optionally substituted sulfonyl groups, optionally substituted sulfoneamide groups, cyano groups, nitro groups, nitroso groups, optionally substituted amidino groups, carboxy groups, alkoxycarbonyl groups of about 2 to 7 carbon atoms, optionally substituted carbamoyl groups, aromatic groups, aromatic heterocyclic groups, and acyl groups (for example, optionally substituted alkylcarbonyl groups, and optionally substituted arylcarbonyl groups). These substituents may be appropriately protected. The protecting group is not particularly limited. Protecting groups suited for hydroxyl groups and amino groups may be appropriately selected from those described in publications, for example, such as Greene et al., Protective Groups in Organic Synthesis, 3rd Edition, 1999, John Wiley & Sons, Inc. The protecting groups may be removed from the product aldehyde or ketone compound after the alcohol oxidation, using appropriate means.

The "co-oxidizing agent" (also referred to as "re-oxidizing agent" or "bulk oxidizing agent") used in the present invention is not particularly limited, as long as it makes the catalyst oxidatively potent, and can oxidize a hydroxylamine to a nitroxyl radical or an oxoammonium salt, or a nitroxyl radical to an oxoammonium salt. Generally, the co-oxidizing agent may be appropriately selected from those used in oxidation reactions that use TEMPO. Examples of such co-oxidizing agents include peroxy acid, hydrogen peroxide, hypohalous acid and salts thereof, perhalic acid and salts thereof, persulfates, halides, halogenating agents (such as N-bromosuccinimide), trihaloisocyanuric acids, (diacetoxyiodo)arenes, oxygen, air, and a mixture of these. Preferred are peracetic acid, m-chloroperbenzoic acid, hydrogen peroxide, sodium hypochlorite, lithium hypochlorite, potassium hypochlorite, calcium hypochlorite, sodium hypobromite, lithium hypobromite, potassium hypobromite, calcium hypobromite, sodium hydrogen persulfate, sodium periodate, periodic acid, trichloroisocyanuric acid, tribromoisocyanuric acid, N-bromosuccinimide, N-chlorosuccinimide, chlorine, bromine, iodine, diacetoxyiodobenzene, oxygen, and air. The method of the present invention can achieve high oxidation efficiency also when air is used as the bulk oxidizing agent, and using air as the bulk oxidizing agent represents a preferred aspect of the present invention.

The oxidation reaction in the present invention may be performed in a solvent or without a solvent. When using a solvent, the solvent is not particularly limited, as long as it does not inhibit the reaction. Examples of such solvents include aliphatic hydrocarbons (such as hexane, heptane, and petroleum ether), aromatic hydrocarbons (such as benzene, toluene, and xylene), nitriles (such as acetonitrile, and propionitrile), halogenated hydrocarbons (such as dichloromethane, chloroform, 1,2-dichloroethane, and carbon tetrachloride), ethers (such as diethyl ether, diisopropyl ether, tetrahydrofuran, dioxane, dimethoxyethane, and diethylene glycol dimethyl ether), amides (such as formamide, dimethylformamide, dimethylacetoamide, and hexamethylphosphoric triamide), sulfoxides (such as dimethylsulfoxide), esters (such as ethyl formate, ethyl acetate, propyl acetate, butyl acetate, and diethyl carbonate), carboxylic acids (such as acetic acid, formic acid, and propionic acid), fluoroalcohols (such as trifluoroethanol, and hexafluoroisopropanol), tertiary alcohols (such as tert-butyl alcohol), sulfolane, and water. These may be used as a mixture. Preferred are aliphatic hydrocarbons, aromatic hydrocarbons, nitriles, halogenated hydrocarbons, esters, carboxylic acids, water, and mixtures of these. Further preferred are dichloromethane, acetonitrile, acetic acid, toluene, ethyl acetate, isopropyl acetate, water, and mixtures of these. Particularly preferred are dichloromethane, acetonitrile, acetic acid, a dichloromethane-water mixed solution, an acetonitrile-water mixed solution, a toluene-water mixed solution, and an ethyl acetate-water mixed solution.

Buffers such as mineral salts and organic salts may be appropriately added to the reaction mixture. Examples of the buffer include alkali metal or alkali earth metal carbonates, alkali metal or alkali earth metal bicarbonates, alkali metal or alkali earth metal hydroxides, alkali metal or alkali earth metal phosphates, and alkali metal or alkali earth metal acetates. Preferred examples include sodium bicarbonate, sodium carbonate, sodium acetate, and phosphates.

Additives that promote reaction may be appropriately added to the reaction mixture. When sodium hypochlorite is used as the co-oxidizing agent for example, the additive may be, for example, a quaternary ammonium salt, or an alkali metal halide, preferably tetrabutylammonium chloride, tetrabutylammonium bromide, sodium bromide, potassium bromide, or a mixture of these. When using oxygen as the co-oxidizing agent, the additive may be typically selected from those used in air oxidation reactions that use TEMPO. Examples of such additives include nitrites, alkyl nitrites, inorganic acids, organic acids, bromine, and transition metals such as copper, iron, and ruthenium. Preferred examples include a mixture of sodium nitrite and acetic acid, a mixture of sodium nitrite and bromine, a mixture of sodium nitrite and iron chloride, copper chloride, and tert-butyl nitrite.

The amount of compound (I) used with respect to the alcohol is not particularly limited, and is typically 0.0001 mol % to 1,000 mol % (0.0001% to 1,000% in terms of the number of moles with respect to the number of moles of the raw material alcohols), preferably 0.0001 mol % to 150 mol %, more preferably 0.001 mol % to 50 mol %, particularly preferably 0.1 mol % to 20 mol % with respect to the alcohols.

The reaction temperature varies with the amounts of the raw material compound, the bulk oxidizing agent, and the reagent used, and is typically −80° C. to 120° C., preferably 0 to 40° C.

The target oxidation product of the reaction may be isolated by isolation procedures such as extraction, recrystallization, and column chromatography after the usual post-processes performed after the reaction.

The oxidation reaction catalyzed by the nitroxyl radical represented by (1) in the present invention is believed to proceed with the same reaction mechanism generally thought to be involved in oxidation reactions catalyzed by TEMPO or AZADO. It follows from this that hydroxylamine products corresponding to the nitroxyl radical represented by (1), and oxoammonium salts are also believed to show the same or similar catalytic activity to that of the nitroxyl radical compounds.

The present invention is described below in greater detail using Examples or the like. It should be noted that the scope of the present invention is not limited by the following.

EXAMPLE 1

Synthesis Method of Compound Represented by Formula (1) with $R^1$=$R^2$=Me (1,5-dimethyl-9-azanoradamantane N-oxyl, hereinafter, "DMN-AZADO")

EXAMPLE 1-1

Synthesis of Heptane-2,6-dione

{Chem. 11}

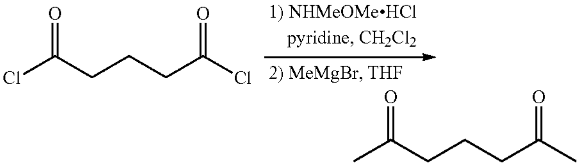

N,O-Dimethylhydroxylamine hydrochloride (42 g, 431 mmol) was added to a dichloromethane (500 ml) solution of glutaryl chloride (25 ml, 196 mmol) at room temperature, and pyridine (95 ml, 1.18 mol) was dropped under ice-cooled condition. After being stirred at room temperature for 2 hours, the reaction mixture was celite filtered. The filtrate was concentrated under reduced pressure, and diethyl ether (300 ml) was added. The mixture was celite filtered again, and concentrated under reduced pressure to give a Weinreb diamide product. The Weinreb diamide product was dissolved in tetrahydrofuran (500 ml), and a 3 M diethyl ether solution (160 ml, 0.470 mol) methylmagnesium bromide was slowly dropped under ice-cooled condition. After being stirred at room temperature for 4 hours, the mixture was brought back to ice-cooled condition, and water was slowly added. After extraction with ethyl acetate, the reaction liquid was washed with saturated brine. The organic layer was dried over magnesium sulfate, and the solvent was evaporated under reduced pressure. The residue was then purified by silica gel column chromatography to give heptane-2,6-dione (20.3 g, 81%).

Heptane-2,6-dione: $^1$H-NMR (400 MHz, $CDCl_3$) δ 2.47 (t, J=7.2 Hz, 4H), 2.13 (s, 6H), (quint, J=7.2 Hz, 2H); $^{13}$C-NMR (100 MHz, $CDCl_3$) δ 208.3, 42.4, 29.9, 17.6; IR (neat, $cm^{-1}$):

2983, 1714, 1357, 1156; MS m/z 128 ($M^+$), 43 (100%); HRMS (EI): calcd for $C_7H_{12}O_2$ 128.0837 ($M^+$), found 128.0835.

EXAMPLE 1-2

Synthesis of 1,5-Dimethyl-9-azabicyclo[3.3.1]nonan-3-one

{Chem. 12}

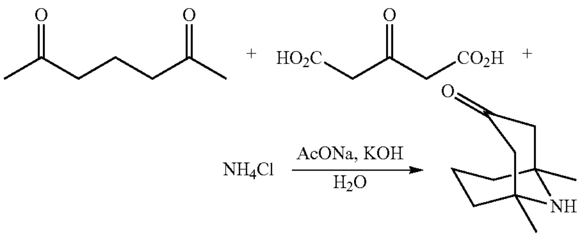

An aqueous solution (32 ml) of heptane-2,6-dione (4.96 g, 38.7 mmol) and acetonedicarboxylic acid (10.74 g, 73.5 mmol) was injected into a sealed tube, and 27 M KOH (6 ml), an ammonium chloride (6.20 g, 116 mmol) aqueous solution (60 ml), and sodium acetate (3.81 g, 46.4 mmol) were added in order under ice-cooled condition. The mixture was then brought to pH 9 with a 1 g/ml KOH aqueous solution. The reaction liquid was stirred inside the sealed tube in the dark at room temperature for 3 days. A 10% hydrochloric acid aqueous solution was slowly dropped until the carbon dioxide gas generation went to completion, and the mixture was washed with dichloromethane. After a separation procedure, the aqueous layer was brought to basic pH with a 10% sodium hydroxide aqueous solution, and extracted with dichloromethane. The organic layer was dried over potassium carbonate, concentrated under reduced pressure, and purified by silica gel column chromatography to give 1,5-dimethyl-9-azabicyclo[3.3.1]nonan-3-one (1.84 g, 28%).

1,5-Dimethyl-9-azabicyclo[3.3.1]nonan-3-one: $^1$H-NMR (400 MHz, $CDCl_3$) δ 2.35 (d, J=16.2 Hz, 2H), 2.11 (d, J=16.2 Hz, 2H), 1.70-1.62 (m, 3H), 1.58-1.41 (m, 1H), 1.41-1.28 (m, 3H), 1.21 (s, 6H); $^{13}$C-NMR (100 MHz, $CDCl_3$) δ 211.3, 52.9, 52.4, 37.9, 31.5, 19.4; IR (neat, $cm^{-1}$): 3285, 3217, 2923, 1704, 1291, 850; MS m/z 167 ($M^+$), 124 (100%); HRMS (EI): calcd for $C_{10}H_{17}NO$ 167.1310 ($M^+$), found 167.1292.

EXAMPLE 1-3

Synthesis of N-tert-Butoxycarbonyl-1,5-dimethyl-9-azabicyclo[3.3.1]nonan-3-one {Chem. 13}

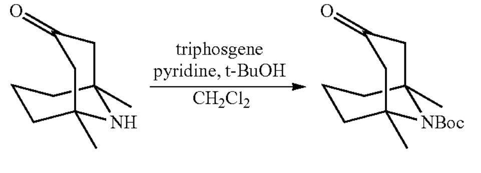

Triphosgene (1.33 g, 4.48 mmol) was added in several portions to a dichloromethane solution (50 ml) of 1,5-dimethyl-9-azabicyclo[3.3.1]nonan-3-one (1.87 g, 11.2 mmol) and pyridine (2.3 ml, 28 mmol) under ice-cooled condition. After stirring the mixture for 30 min under ice-cooled condition, tert-butanol (2.2 ml, 22.4 mmol) was dropped, and the mixture was stirred for 8 h. The reaction was stopped by adding water to the reaction liquid. The reaction liquid was then extracted with diethyl ether, washed with saturated brine, dried over magnesium sulfate, and concentrated under reduced pressure. The residue was purified by silica gel column chromatography, and N-tert-butoxycarbonyl-1,5-dimethyl-9-azabicyclo[3.3.1]nonan-3-one (0.37 g, 13%), and 1,5-dimethyl-9-azabicyclo[3.3.1]nonan-3-one (1.1 g, 59%) were collected. The collected 1,5-dimethyl-9-azabicyclo[3.3.1]nonan-3-one was subjected to the same procedure twice to give N-tert-butoxycarbonyl-1,5-dimethyl-9-azabicyclo[3.3.1]nonan-3-one (1.36 g, 44%).

N-tert-Butoxycarbonyl-1,5-dimethyl-9-azabicyclo[3.3.1]nonan-3-one: $^1$H-NMR (400 MHz, $CDCl_3$) δ 2.65 (d, J=15.5 Hz, 2H), 2.26 (d, J=16.9 Hz, 2H), 1.78-1.70 (m, 2H), 1.59-1.51 (m, 13H), 1.39 (s, 6H); $^{13}$C-NMR (100 MHz, $CDCl_3$) δ 210.5, 158.9, 81.2, 57.1, 50.5, 38.8, 29.8, 28.0, 19.1; IR (neat, $cm^{-1}$): 1704, 1366, 1306, 1272; MS m/z 267 ($M^+$), 57 (100%); HRMS (EI): calcd for $C_{15}H_{25}NO_3$ 267.1834 ($M^+$), found 267.1818.

EXAMPLE 1-4

Synthesis of N-tert-Butoxycarbonyl-1,5-dimethyl-3-(tosylhydrazono)-9-azabicyclo[3.3.1]nonane {Chem. 14}

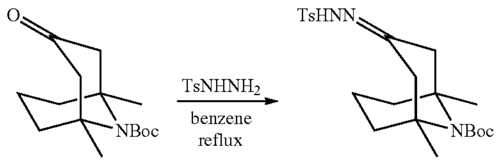

p-Toluenesulfonyl hydrazine (6.37 g, 34.2 mmol) was added to a benzene solution (115 ml) of N-tert-butoxycarbonyl-1,5-dimethyl-9-azabicyclo[3.3.1]nonan-3-one (3.04 g, 11.4 mmol), and the mixture was heated under reflux for 6 h with a Dean-Stark device. After adding saturated sodium bicarbonate water under ice-cooled condition, the ice-cooled reaction liquid was extracted with ethyl acetate, washed with saturated brine, and dried over magnesium sulfate. After concentration under reduced pressure, the residue was purified by silica gel column chromatography to give N-tert-butoxycarbonyl-1,5-dimethyl-3-(tosylhydrazono)-9-azabicyclo[3.3.1]nonane (3.07 g, 62%).

N-tert-Butoxycarbonyl-1,5-dimethyl-3-(tosylhydrazono)-9-azabicyclo[3.3.1]nonane: $^1$H-NMR (400 MHz, $CDCl_3$) δ 7.85 (d, J=7.7 Hz, 2H), 7.42 (br s, 1H), 7.30 (d, J=7.7 Hz, 2H), 2.53-2.22 (m, 4H), 2.42 (s, 3H), 1.74-1.60 (m, 2H), 1.60-1.35 (m, 4H), 1.44 (s, 9H), 1.32 (s, 3H), 1.30 (s, 3H); $^{13}$C-NMR (100 MHz, $CDCl_3$) δ 161.1, 158.6, 143.8, 135.6, 129.4, 127.8, 80.9, 56.2, 55.4, 43.5, 39.2, 38.1, 36.2, 30.3, 29.9, 27.9, 21.5, 18.8; IR (neat, $cm^{-1}$): 2930, 1697, 1166, 1137; MS m/z 435 ($M^+$), 180 (100%); HRMS (EI): calcd for $C_{22}H_{33}N_3O_4S$ 435.2192 ($M^+$), found 435.2206.

EXAMPLE 1-5

Synthesis of N-tert-Butoxycarbonyl-1,5-dimethyl-9-azanoradamantane

{Chem. 15}

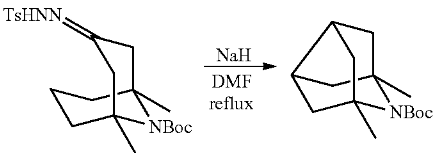

Sodium hydride (18.9 mg, 0.466 mmol) was added to a dimethylformamide solution (1 ml) of N-tert-butoxycarbonyl-1,5-dimethyl-3-(tosylhydrazono)-9-azabicyclo[3.3.1]nonane (40.6 mg, 93.2 μmol) at room temperature. The mixture was stirred for 15 min at room temperature, and heated under reflux for 15 min. After adding water under ice-cooled condition, the ice-cooled reaction liquid was extracted with diethyl ether, washed with saturated brine, dried over magnesium sulfate, and concentrated under reduced pressure. The residue was then purified by silica gel column chromatography to give N-tert-butoxycarbonyl-1,5-dimethyl-9-azanoradamantane (13.6 mg, 58%).

N-tert-Butoxycarbonyl-1,5-dimethyl-9-azanoradamantane: $^1$H-NMR (400 MHz, $CDCl_3$) δ 2.61 (quint m, J=5.4 Hz, 2H), 1.76 (d, J=10.1 Hz, 4H), 1.57-1.48 (m, 4H), 1.48 (s, 9H), 1.38 (s, 6H); $^{13}$C-NMR (100 MHz, $CDCl_3$) δ 159.8, 80.2, 65.8, 48.3, 38.8, 28.1, 24.2; IR (neat, $cm^{-1}$): 2926, 2857, 1698, 1351, 1149; MS m/z 251 ($M^+$), 195 (100%); HRMS (EI): calcd for $C_{15}H_{25}NO_2$ 251.1885 ($M^+$), found 251.1895.

EXAMPLE 1-5-2

Synthesis of 1,5-Dimethyl-9-azanoradamantane N-oxyl (DMN-AZADO)

{Chem. 16}

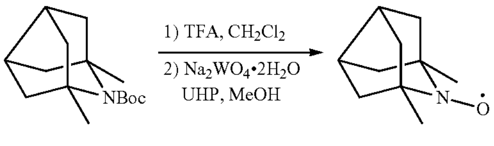

Trifluoroacetic acid (0.56 ml, 6.0 mmol) was dropped onto a dichloromethane solution (7.5 ml) of N-tert-butoxycarbonyl-1,5-dimethyl-9-azanoradamantane (376 mg, 1.50 mmol) under ice-cooled condition. The mixture was stirred at room temperature for 1 h, and water was added. After extraction with dichloromethane, the organic layer was dried over potassium carbonate, and concentrated under reduced pressure. To a methanol solution (3.0 ml) of the resulting 1,5-dimethyl-9-azanoradamantane was then added sodium tungstate dihydrate (247 mg, 0.75 mmol), and the mixture was stirred at room temperature for 30 min. The mixture was further stirred at room temperature for 40 min after adding urea.hydrogen peroxide (urea peroxide or UHP (urea hydrogen peroxide); 564 mg, 6.0 mmol). This was followed by addition of saturated sodium bicarbonate water, and extraction with diethyl ether. The organic layer was washed with saturated brine, dried over magnesium sulfate, and concentrated under reduced pressure. The residue was then purified by silica gel column chromatography to give 1,5-dimethyl-9-azanoradamantane N-oxyl (DMN-AZADO; 69 mg, 28%).

DMN-AZADO: IR (neat, $cm^{-1}$): 2955, 2869, 1732, 1456, 1374, 1337; MS m/z 166 ($M^+$), 93 (100%); HRMS (EI): calcd for $C_{10}H_{16}NO$ 166.1232 ($M^+$), found 166.1232; Anal: calcd for $C_{10}H_{16}NO$: C, 72.25; H, 9.70; N, 8.43. found: C, 71.91; H, 9.61; N, 8.07.

EXAMPLE 2

The DMN-AZADO synthesized above, and the existing nitroxyl radical oxidation catalysts TEMPO and 1-Me-AZADO were compared and examined for their catalytic activity in selective oxidation reactions of primary alcohol. The reactions were performed by using sodium hypochlorite as the co-oxidizing agent.

TABLE 1

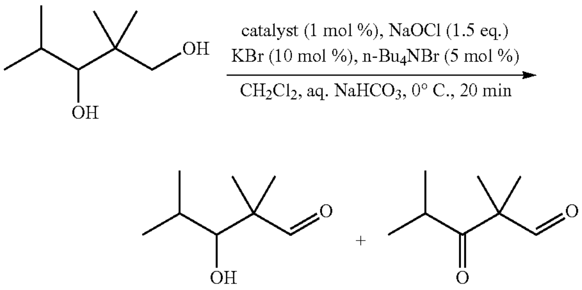

hydroxyaldehyde ketoaldehyde

| | | yield | | |
|---|---|---|---|---|
| entry | catalyst | hydroxyaldehyde | ketoaldehyde | SM |
| 1 | TEMPO | 69% | 17% | 0% |
| 2 | 1-Me-AZADO | 70% | 0% | 24% |
| 3 | DMN-AZADO | 94% | trace | 0% |

With 1.5 equivalents of sodium hypochlorite, 17% of the product was collected as an unreacted raw material in the reaction using TEMPO, whereas 24% of the product of the reaction using 1-Me-AZADO was a diketone product resulting from the oxidation of both the primary alcohol and the secondary alcohol. In contrast to these moderate yields in the reactions catalyzed by TEMPO and 1-Me-AZADO, the reaction using the DMN-AZADO produced the target hydroxyketone product in high yield at 94%. These results demonstrated that the DMN-AZADO functions as an alcohol oxidation reaction catalyst capable of oxidizing primary alcohol with high selectivity and reactivity.

The reactivity of DMN-AZADO for various diols was examined by comparison to TEMPO.

TABLE 2

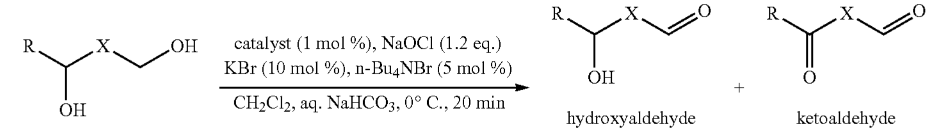

hydroxyaldehyde + ketoaldehyde

| substrate | catalyst | time | yield: hydroxyaldehyde | yield: ketoaldehyde | yield: SM |
|---|---|---|---|---|---|
| 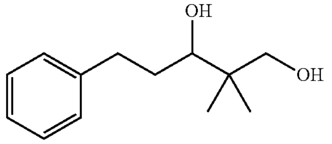 | TEMPO | 20 min | 70% | 0% | 7% |
| | DMN-AZADO | 4 min | 93% | trace | trace |
| 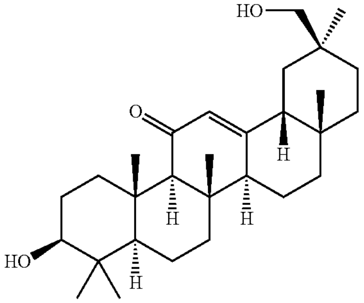 | TEMPO | 20 min | 78% | 0% | 8% |
| | DMN-AZADO | 3 min | 91% | trace | trace |
| 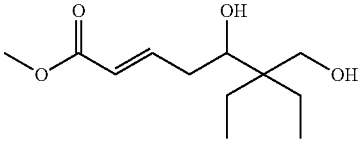 [SMILES: CCC(CC)(CO)C(O)C/C=C/C(=O)OC] | TEMPO | 20 min | 67% | 0% | 17% |
| | DMN-AZADO | 10 min | 90% | 0% | 0% |

The yield of the target hydroxyketone product was only about 67 to 78% in 20 minutes of reactions with TEMPO, though the yield varied for different substrates. On the other hand, the reactions using DMN-AZADO produced the target hydroxyketone product in 90% or higher yield with different substrates, and the non-target compounds, including ketoaldehyde, were within limits of error. These results demonstrated that the DMN-AZADO functions as an alcohol oxidation reaction catalyst capable of more efficiently oxidizing primary alcohol with higher selectivity and reactivity than TEMPO, irrespective of the substrate.

EXAMPLE 2-1

Oxidation of (E)-Methyl 6-ethyl-5-hydroxy-6-(hydroxymethyl)-2-octenate

{Chem. 17}

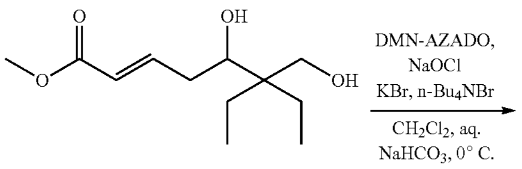

-continued

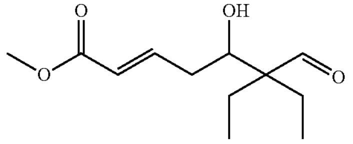

A saturated sodium bicarbonate aqueous solution (350 μl) of DMN-AZADO (0.367 mg, 2.2 μmol), potassium bromide (2.63 mg, 22 μmol), and tetrabutylammonium bromide (3.56 mg, 11 μmol) was added to a dichloromethane solution (0.59 ml) of (E)-methyl 6-ethyl-5-hydroxy-6-(hydroxymethyl)-2-octenate (51.0 mg, 0.221 mmol), and the mixture was ice cooled to 0° C. Thereafter, a mixed solution of a sodium hypochlorite aqueous solution (1.262 M, 210 μl) and a saturated sodium bicarbonate aqueous solution (240 μl) was dropped, and the mixture was stirred at 0° C. for 10 min. This was followed by addition of a 20% sodium thiosulfate aqueous solution (1 ml), and extraction with diethyl ether. The organic layer was washed with saturated brine, and dried over sodium sulfate. The solvent was evaporated under reduced pressure. The resulting residue was then purified by silica gel column chromatography to obtain the desired compound (45.6 mg, 90%).

(E)-Methyl 6-Ethyl-6-formyl-5-hydroxy-2-octenate: $^1$H-NMR (400 MHz, $CDCl_3$) δ 9.63 (s, 1H), 7.03 (ddd, J=14.4 Hz, 7.2 Hz, 7.2 Hz, 1H), 5.94 (d, J=14.4 Hz, 1H), 3.98 (ddd, J=10.4 Hz, 4.8 Hz, 2.4 Hz, 1H), 3.74 (s, 3H), 2.44-2.21 (m, 2H), 2.29 (d, J=4.8 Hz, 1H), 1.80 (dq, J=14.8 Hz, 7.4 Hz, 1H), 1.78 (dq, J=14.8 Hz, 7.4 Hz, 1H), 1.70 (dq, J=14.8 Hz, 7.4 Hz, 1H), 1.58 (dq, J=14.8 Hz, 7.4 Hz, 1H), 0.94 (t, J=7.4 Hz, 3H), 0.87 (t, J=7.4 Hz, 3H); $^{13}$C-NMR (100 MHz, $CDCl_3$) δ 208.2, 166.7, 146.2, 123.3, 72.0, 55.4, 51.5, 34.6, 23.0, 22.0, 8.27, 7.97; IR (neat, $cm^{-1}$): 3500, 2969, 2883, 1722, 1658, 1438, 1328, 1275, 1219, 1170, 1043, 978; MS m/z 229 ($M^+$+H), 100 (100%); HRMS (EI) calcd for $C_{12}H_{21}O_4$ 229.1434 ($M^+$+H), found 229.1426.

EXAMPLE 2-2

Oxidation of 2,2-Dimethyl-5-phenylpentane-1,3-diol

{Chem. 18}

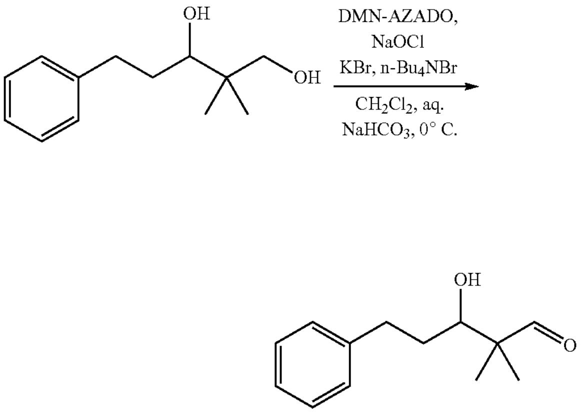

2,2-Dimethyl-5-phenylpentane-1,3-diol (42.5 mg, 0.204 mmol) was oxidized in the same manner as in Example 2-1 to give 3-hydroxy-2,2-dimethyl-5-phenylpentanal (39.3 mg, 93%).

3-Hydroxy-2,2-dimethyl-5-phenylpentanal: $^1$H-NMR (400 MHz, $CDCl_3$) δ 9.51 (s, 1H), 7.36-7.17 (m, 5H), 3.77 (d, J=9.7 Hz, 1H), 2.96 (ddd, J=14.0 Hz, 9.7 Hz, 5.4 Hz, 1H), 2.67 (ddd, J=14.0 Hz, 9.2 Hz, 7.3 Hz, 1H), 2.29 (br s, 1H), 1.83-1.64 (m, 2H), 1.11 (s, 3H), 1.04 (s, 3H); $^{13}$C-NMR (100 MHz, $CDCl_3$) δ 206.6, 141.6, 128.3, 125.8, 74.0, 50.3, 33.0, 32.5, 18.8, 16.3; IR (neat, $cm^{-1}$): 3466, 2959, 2871, 1721, 1455, 1075, 1046, 700; MS m/z 188 ($M^+$-$H_2O$), 72 (100%); HRMS (EI) calcd for $C_{13}H_{16}O$ 188.1201 ($M^+$-$H_2O$), found 188.1189.

EXAMPLE 2-3

Oxidation of Olean-12-ene-11-oxo-3β,30-diol

{Chem. 19}

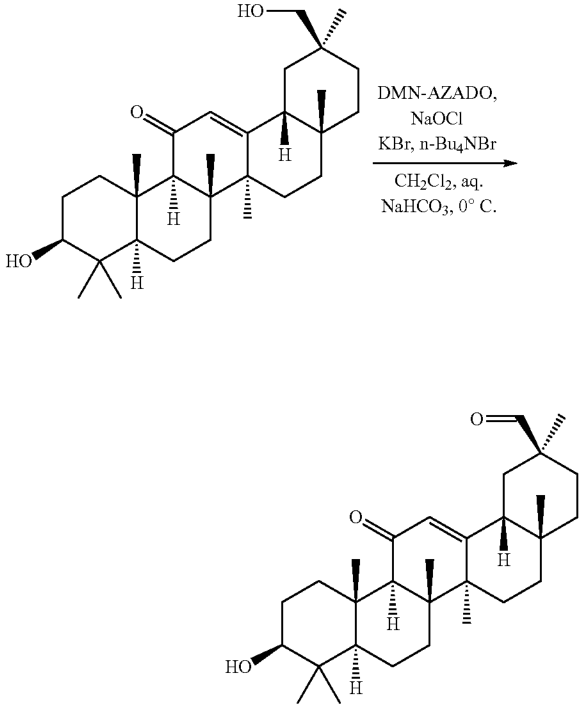

Olean-12-ene-11-oxo-3β,30-diol (41.2 mg, 0.090 mmol) was oxidized in the same manner as in Example 2-1 to give the desired compound (37.3 mg, 91%).

Olean-12-ene-3β-hydroxy-11-oxo-30-al: $^1$H-NMR (400 MHz, $CDCl_3$) δ 9.42 (s, 1H), 5.66 (s, 1H), 3.23 (dd, J=10.6 Hz, 5.3 Hz, 1H), 2.79 (dt, J=13.6 Hz, 3.4 Hz, 1H), 2.34 (s, 1H), 2.14-1.96 (m, 2H), 1.96-1.77 (m, 3H), 1.77-1.52 (m, 6H), 1.52-1.34 (m, 7H), 1.34-1.09 (m, 8H), 1.09-0.90 (m, 8H), 0.81 (s, 3H), 0.80 (s, 3H), 0.70 (d, J=10.6 Hz, 1H); $^{13}$C-NMR (100 MHz, $CDCl_3$) δ 205.6, 200.0, 168.5, 128.6, 78.7, 61.8, 54.9, 47.6, 46.8, 45.4, 43.2, 39.13, 39.11, 38.4, 37.1, 32.7, 31.9, 28.5, 28.3, 28.1, 27.3, 26.4, 26.1, 24.0, 23.7, 18.7, 17.5, 16.3, 15.5; IR (neat, $cm^{-1}$): 3461, 2927, 2864, 1728, 1655, 1456, 1387, 1209, 1075, 755; MS m/z 454 ($M^+$), 287 (100%); HRMS (EI) calcd for $C_{30}H_{46}O_3$ 454.3447 ($M^+$), found 454.3436.

EXAMPLE 3

DMN-AZADO, TEMPO, 1-Me-AZADO, and AZADO were compared for catalytic activity under the conditions in which natural product betulin and diacetoxyiodobenzene were used as a substrate and a co-oxidizing agent, respectively. The existing oxidizing agent DMP (Dess-Martin periodinane) was also examined for comparison.

TABLE 3

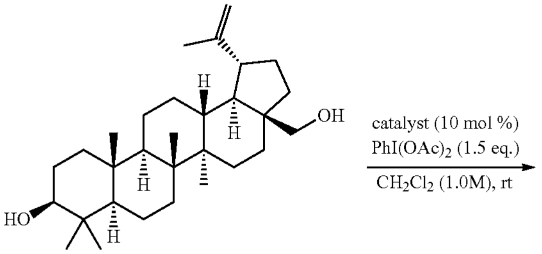

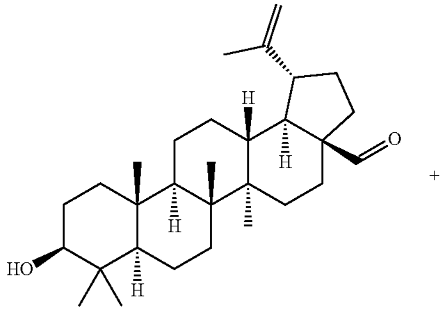

hydroxyaldehyde

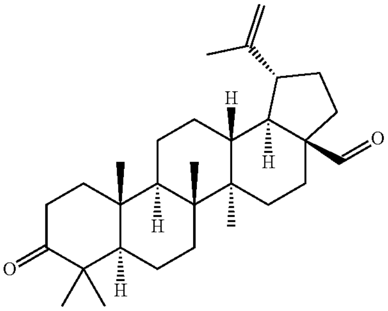

ketoaldehyde

| entry | catalyst | time | yield: hydroxy-aldehyde | yield: keto-aldehyde | yield: SM |
|---|---|---|---|---|---|
| 1 | TEMPO | 2 h | 56% | 0% | 26% |
| 2 | 1-Me-AZADO | 15 min | 49% | 51% | 0% |
| 3 | AZADO | 15 min | 48% | 46% | 0% |
| 4 | DMN-AZADO | 45 min | 97% | 3% | 0% |
| 5 | DMP (1.5 eq.)[a] | 3 h | 8% | 13% | 61% |

[a]no use of $PhI(OAc)_2$, $CH_2Cl_2$ (0.1M)

The reactions using AZADO and 1-Me-AZADO yielded the diketone product in about 50%, whereas 26% of the raw material was collected after 2 hours of reaction with TEMPO. Over an extended reaction time, a decomposition reaction of the target product hydroxyaldehyde proceeded with TEMPO. On the other hand, the reaction with DMN-AZADO produced the target hydroxyaldehyde in high yield, though only a slight generation (3%) of diketone product was observed. Selectivity was not observed for DMP.

It was found from these results that the DMN-AZADO had higher reactivity than TEMPO, and higher primary alcohol selectivity than AZADO and 1-Me-AZADO even when used with the co-oxidizing agent diacetoxyiodobenzene.

EXAMPLE 4

The catalytic activity of TEMPO and DMN-AZADO was examined in greater detail with various catalytic amounts under the conditions in which betulin and diacetoxyiodobenzene were used as a substrate and a co-oxidizing agent, respectively.

TABLE 4

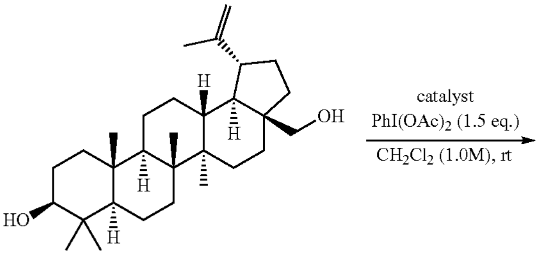

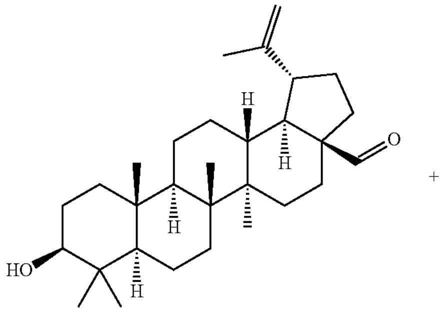

hydroxyaldehyde

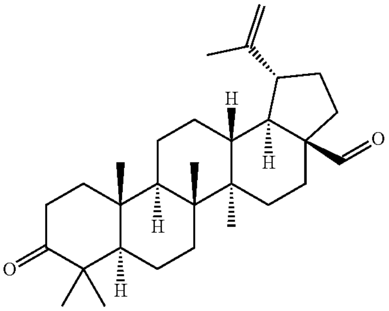

ketoaldehyde

| entry | cataVst | loading amount (mol %) | time | yield: hydroxy-aldehyde | yield: keto-aldehyde | yield: SM |
|---|---|---|---|---|---|---|
| 1 | TEMPO | 10 | 2 h | 56% | 0% | 26% |
| 2 | | 20 | 3.5 h | 98% | 0% | 0% |
| 3 | | 15 | 5.5 h | 93% | 0% | 6% |
| 4 | DMN- | 10 | 0.75 h | 97% | 3% | 0% |
| 5 | AZADO | 5 | 1 h | 92% | 2% | 0% |
| 6 | | 3 | 1.3 h | 94% | 0% | 5% |

The primary alcohol selective reactions efficiently proceeded with TEMPO when the catalytic amount was increased to 15 mol %, whereas the reactions using DMN-AZADO efficiently proceeded with a catalytic amount as low as 3 mol %. DMN-AZADO advantageously afforded a shorter reaction time than TEMPO. DMN-AZADO was clearly more advantageous than TEMPO in terms of catalytic amount and reaction time.

EXAMPLE 5

The reactivity of DMN-AZADO for various diols was examined by comparison to TEMPO.

The primary alcohol selective oxidation reactions of various diols were faster, and more efficient with DMN-AZADO than with TEMPO. The primary alcohol oxidation at the neopentyl position also proceeded faster with DMN-AZADO, demonstrating that DMN-AZADO is a high-activity primary alcohol selective oxidation catalyst.

TABLE 5

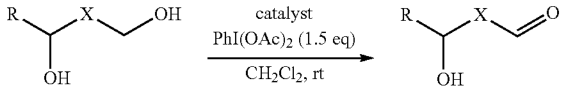

| entry | substrate | loading amount (mol %) | yield/time TEMPO | DMN-AZADO |
|---|---|---|---|---|
| 1 | 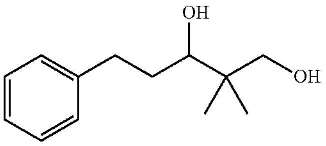 | 5 | 26%/1.5 h | 92%/15 min |
| 2 | 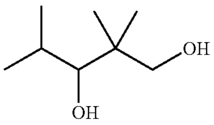 | 5 | 21%/2 h | 80%/1 h |
| 3[a] | 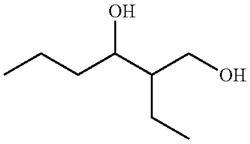 | 2 | 58%/4 h | 85%/3 h |
| 4[a] | 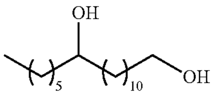 | 2 | 78%/2.5 h | 79%/2 h |
| 5 | 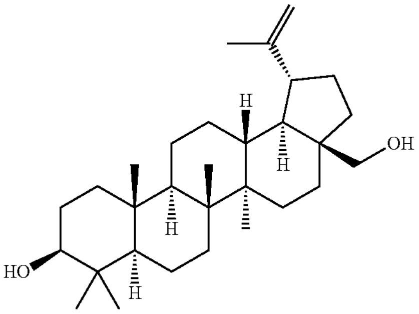 | 5 | 32%/4 h | 92%/1 h |
| 6 | 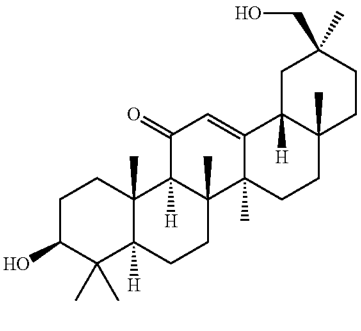 | 5 | 62%/2 h | 99%/1 h |

TABLE 5-continued

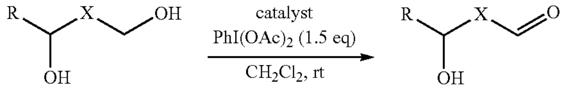

| entry | substrate | loading amount (mol %) | yield/time TEMPO | yield/time DMN-AZADO |
|---|---|---|---|---|
| 7 | 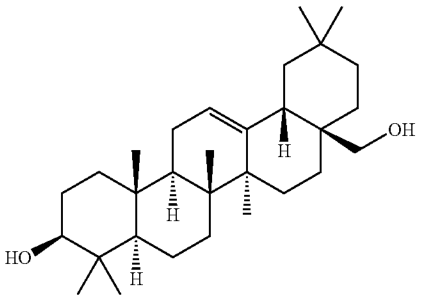 | 5 | 41%/2.5 h | 95%/30 min |

[a]1.2 eq. $PhI(OAc)_2$ was used.

EXAMPLE 6

Primary Alcohol Selective Oxidation Reaction Using Diacetoxyiodobenzene as Co-Oxidizing Agent

EXAMPLE 6-1

{Chem. 20}

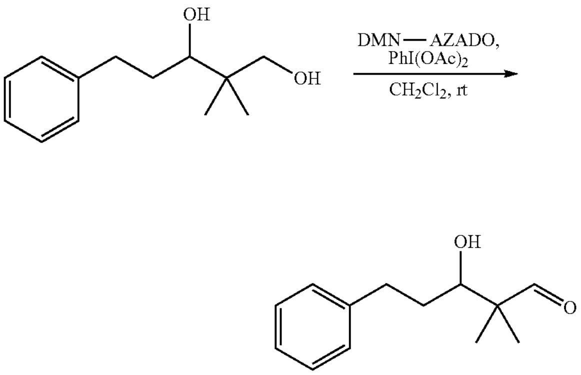

DMN-AZADO (2.00 mg, 0.012 mmol) and diacetoxyiodobenzene (117 mg, 0.362 mmol) were added to a dichloromethane solution (0.24 ml) of 2,2-dimethyl-5-phenylpentane-1,3-diol (50.2 mg, 0.241 mmol), and the mixture was stirred at room temperature for 15 min. This was followed by addition of saturated sodium bicarbonate water (1 ml) and a sodium thiosulfate solution (1 ml), and extraction with diethyl ether. The organic layer was washed with saturated brine, and dried over magnesium sulfate. The solvent was evaporated under reduced pressure. The resulting residue was then purified by silica gel column chromatography to give 3-hydroxy-2,2-dimethyl-5-phenylpentanal (49.2 mg, 92%).

3-Hydroxy-2,2-dimethyl-5-phenylpentanal: $^1$H-NMR (400 MHz, $CDCl_3$) δ 9.51 (s, 1H), 7.36-7.17 (m, 5H), 3.77 (d, J=9.7 Hz, 1H), 2.96 (ddd, J=14.0 Hz, 9.7 Hz, 5.4 Hz, 1H), 2.67 (ddd, J=14.0 Hz, 9.2 Hz, 7.3 Hz, 1H), 2.29 (br s, 1H), 1.83-1.64 (m, 2H), 1.11 (s, 3H), 1.04 (s, 3H); $^{13}$C-NMR (100 MHz, $CDCl_3$) δ 206.6, 141.6, 128.3, 125.8, 74.0, 50.3, 33.0, 32.5, 18.8, 16.3; IR (neat, $cm^{-1}$): 3466, 2959, 2871, 1721, 1455, 1075, 1046, 700; MS m/z 188 ($M^+$-$H_2O$), 72 (100%); HRMS (EI) calcd for $C_{13}H_{16}O$ 188.1201 ($M^+$-$H_2O$), found 188.1189.

EXAMPLE 6-2

Oxidation of 2,2,4-Trimethylpentane-1,3-diol

{Chem. 21}

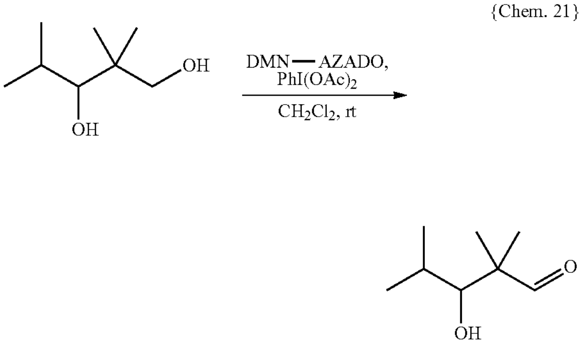

2,2,4-Trimethylpentane-1,3-diol (41.7 mg, 0.285 mmol) was oxidized in the same manner as in Example 6-1 to give 3-hydroxy-2,2,4-trimethylpentanal (32.8 mg, 80%).

3-Hydroxy-2,2,4-trimethylpentanal: $^1$H-NMR (400 MHz, $CDCl_3$) δ 9.63 (s, 1H), 3.55 (dd, J=5.8 Hz, 3.9 Hz, 1H), 1.96 (d, J=5.8 Hz, 1H), 1.88 (sept d, J=6.8 Hz, 3.9 Hz, 1H), 1.13 (s, 3H), 1.12 (s, 3H), 0.97 (d, J=6.8 Hz, 3H), 0.91 (d, J=6.8 Hz, 3H); $^{13}$C-NMR (100 MHz, $CDCl_3$) δ 206.5, 80.3, 30.0, 21.8, 19.9, 18.7, 17.3; IR (neat, $cm^{-1}$): 3483, 1713; MS m/z 145

($M^{+}$+H), 127 (100%); HRMS (FAB) calcd for $C_8H_{17}O_2$ 145.1229 ($M^{+}$+H), found 145.1218.

EXAMPLE 6-3

Oxidation of 2-Ethylhexane-1,3-diol

{Chem. 22}

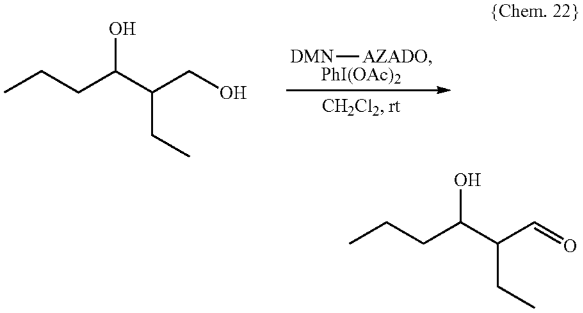

2-Ethylhexane-1,3-diol (51.7 mg, 0.354 mmol) was oxidized in the same manner as in Example 6-1 using diacetoxyiodobenzene (137 mg, 0.425 mmol) to give the desired compound (43.2 mg, 85%).

2-Ethyl-3-hydroxyhexanal: $^{1}$H-NMR (400 MHz, $CDCl_3$) δ9.78 (d, J=2.4 Hz, 0.4H), 9.76 (d, J=2.9 Hz, 0.6H), 3.98 (dt, J=8.7 Hz, 4.4 Hz, 0.4H), 3.88 (dt, J=5.8 Hz, 5.8 Hz, 0.6H), 2.37-2.23 (m, 1H), 2.06 (br s, 0.6H), 1.86 (br s, 0.4H), 1.84-1.73 (m, 1H), 1.73-1.61 (m, 1H), 1.58-1.42 (m, 3H), 1.42-1.29 (m, 1H), 1.05-0.89 (m, 6H); $^{13}$C-NMR (100 MHz, $CDCl_3$) δ major 205.9, 70.8, 58.7, 37.1, 19.3, 18.6, 13.8, 11.4, minor 205.7, 70.5, 58.8, 36.5, 19.1, 17.4, 13.8, 12.1; IR (neat, $cm^{-1}$): 3428, 2961, 2874, 1719, 1463, 1142, 978; MS m/z 145 ($M^{+}$+H), 72 (100%); HRMS (EI) calcd for $C_8H_{17}O_2$ 145.1229 ($M^{+}$+H), found 145.1215.

EXAMPLE 6-4

Oxidation of Octadecane-1,12-diol

{Chem. 23}

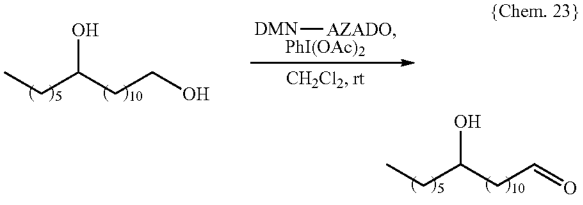

Octadecane-1,12-diol (51.7 mg, 0.180 mmol) was oxidized in the same manner as in Example 6-1 to give the desired compound (40.2 mg, 79%).

12-Hydroxyoctadecanal: mp 53-54° C. ($Et_2O$-hexane); $^{1}$H-NMR (400 MHz, $CDCl_3$) δ 9.76 (t, J=1.8 Hz, 1H), 3.58 (brs, 1H), 2.42 (td, J=7.2 Hz, 1.8 Hz, 2H), 1.63 (quint, J=7.2 Hz, 2H), 1.49-1.30 (m, 6H), 1.42-1.20 (m, 21H), 0.88 (t, J=6.5 Hz, 3H); $^{13}$C-NMR (100 MHz, $CDCl_3$) δ 202.9, 71.8, 43.8, 37.41, 37.38, 31.8, 29.6, 29.5, 29.4, 29.31, 29.25, 29.1, 25.6, 25.5, 22.5, 22.0, 14.0; IR (neat, $cm^{-1}$): 3300, 3211, 2913, 2848, 1712, 1469, 1130, 1079, 719; MS m/z 283 ($M^{+}$-H), 199 (100%); HRMS (EI) calcd for $C_{18}H_{35}O_2$ 283.2637 ($M^{+}$-H), found 283.2622.

EXAMPLE 6-5

Oxidation of Betulin

{Chem. 24}

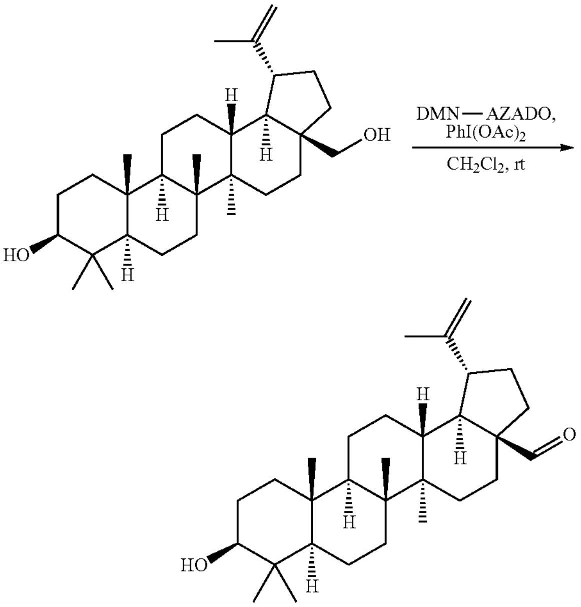

Betulin (50.4 mg, 0.114 mmol) was oxidized in the same manner as in Example 6-1 to give the desired compound (46.0 mg, 92%).

Betulinal: mp 168-169° C. ($CHCl_3$-hexane); $^{1}$H-NMR (400 MHz, $CDCl_3$) δ 9.68 (s, 1H), 4.76 (s, 1H), 4.63 (s, 1H), 3.18 (dd, J=10.6 Hz, 4.4 Hz, 1H), 2.86 (td, J=11.1 Hz, 5.8 Hz, 1H), 2.12-2.04 (m, 1H), 2.02 (td, J=12.1 Hz, 3.4 Hz, 1H), 1.96-1.82 (m, 1H), 1.82-0.84 (m, 35H), 0.82 (s, 3H), 0.75 (s, 3H), 0.67 (d, J=9.1 Hz, 1H); $^{13}$C-NMR (100 MHz, $CDCl_3$) δ 206.7, 149.7, 110.1, 78.9, 59.3, 55.3, 50.4, 48.0, 47.5, 42.5, 40.8, 38.8, 38.71, 38.67, 37.2, 34.3, 33.2, 29.8, 29.2, 28.8, 28.0, 27.4, 25.5, 20.7, 19.0, 18.2, 16.1, 15.9, 15.3, 14.2; IR (neat, $cm^{-1}$): 3419, 2942, 2868, 1724, 1452, 1377, 910, 733; MS m/z 440 ($M^{+}$), 440 (100%); HRMS (EI) calcd for $C_{30}H_{48}O_2$ 440.3654 ($M^{+}$), found 440.3656.

EXAMPLE 6-6

Oxidation of Olean-12-ene-11-oxo-3β,30-diol

{Chem. 25}

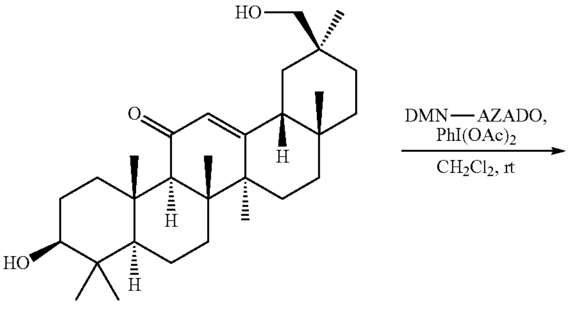

-continued

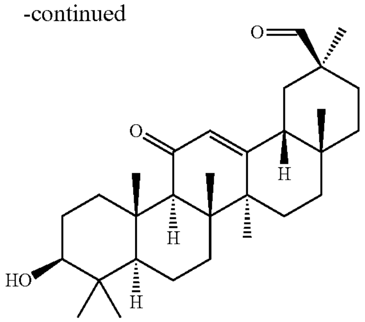

Olean-12-ene-11-oxo-3β,30-diol (43.4 mg, 0.095 mmol) was oxidized in the same manner as in Example 6-1 to give the desired compound (42.8 mg, 99%).

Olean-12-ene-3β-hydroxy-11-oxo-30-al: $^1$H-NMR (400 MHz, $CDCl_3$) δ 9.42 (s, 1H), 5.66 (s, 1H), 3.23 (dd, J=10.6 Hz, 5.3 Hz, 1H), 2.79 (dt, J=13.6 Hz, 3.4 Hz, 1H), 2.34 (s, 1H), 2.14-1.96 (m, 2H), 1.96-1.77 (m, 3H), 1.77-1.52 (m, 6H), 1.52-1.34 (m, 7H), 1.34-1.09 (m, 8H), 1.09-0.90 (m, 8H), 0.81 (s, 3H), 0.80 (s, 3H), 0.70 (d, J=10.6 Hz, 1H); $^{13}$C-NMR (100 MHz, $CDCl_3$) δ 205.6, 200.0, 168.5, 128.6, 78.7, 61.8, 54.9, 47.6, 46.8, 45.4, 43.2, 39.13, 39.11, 38.4, 37.1, 32.7, 31.9, 28.5, 28.3, 28.1, 27.3, 26.4, 26.1, 24.0, 23.7, 18.7, 17.5, 16.3, 15.5; IR (neat, $cm^{-1}$): 3461, 2927, 2864, 1728, 1655, 1456, 1387, 1209, 1075, 755; MS m/z 454 ($M^+$), 287 (100%); HRMS (EI) calcd for $C_{30}H_{46}O_3$454.3447 ($M^+$), found 454.3436.

EXAMPLE 6-7

Oxidation of Erythrodiol

{Chem. 26}

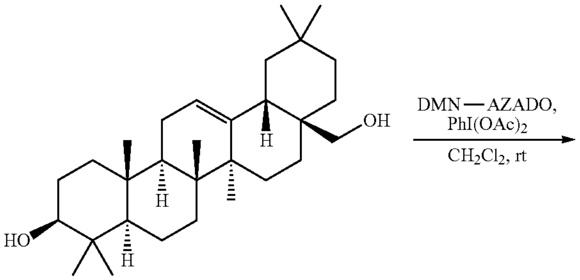

-continued

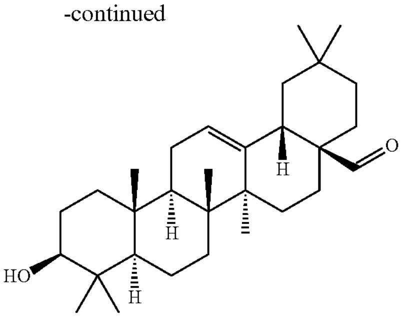

Erythrodiol (44.0 mg, 0.099 mmol) was oxidized in the same manner as in Example 6-1 to give the desired compound (41.7 mg, 95%).

Oleanoaldehyde: [a $]_D^{22}$+68.7 (c 0.41, $CHCl_3$); mp 184-185° C. ($CHCl_3$-hexane); $^1$H-NMR (400 MHz, $CDCl_3$) δ 9.40 (s, 1H), 5.34 (t, J=3.5 Hz, 1H), 3.21 (dd, J=11.2 Hz, 4.4 Hz, 1H), 2.63 (dd, J=13.7 Hz, 4.4 Hz, 1H), 1.98 (td, J=13.6 Hz, 3.9 Hz, 1H), 1.89 (t, J=3.9 Hz, 1H), 1.87 (m, 1H), 1.80-0.60 (m, 41H); $^{13}$C-NMR (100 MHz, $CDCl_3$) δ 207.5, 142.9, 123.2, 78.9, 55.2, 49.1, 47.5, 45.6, 41.7, 40.4, 39.5, 38.7, 38.4, 37.0, 33.1, 33.0, 32.7, 30.6, 28.1, 27.7, 27.1, 26.7, 25.5, 23.40, 23.38, 22.1, 18.3, 17.0, 15.6, 15.3; IR (neat, $cm^{-1}$): 3509, 2928, 2859, 1712, 1462, 1049, 1029, 997, 753; MS m/z 440 ($M^+$), 203 (100%); HRMS (EI) calcd for $C_{30}H_{48}O_2$ 440.3654 ($M^+$), found 440.3649.

EXAMPLE 7

TEMPO and DMN-AZADO were compared and examined for catalyst efficiency and primary alcohol selectivity in the one-pot oxidation reaction of primary alcohol into carboxylic acid performed in the presence of a catalytic amount of sodium hypochlorite, and sodium chlorite used as a co-oxidizing agent.

TABLE 6

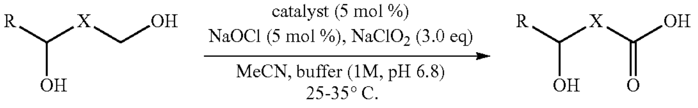

| entry | substrate | yield/time TEMPO | yield/time DMN-AZADO |
|---|---|---|---|
| 1 | 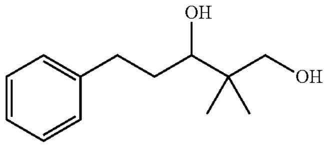 | 50%/24 h | 91%/3 h |

TABLE 6-continued

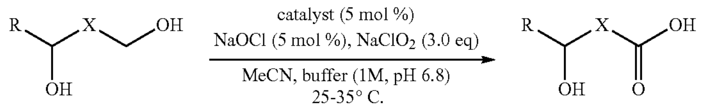

| entry | substrate | yield/time TEMPO | yield/time DMN-AZADO |
|---|---|---|---|
| 2 | 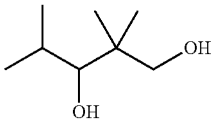 | 49%/24 h | 92%/7 h |
| 3 | 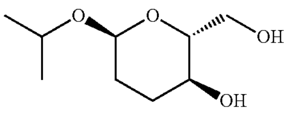 | 81%/24 h | 95%/12 h |
| 4 | 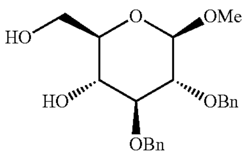 [SMILES: CO[C@@H]1O[C@H](CO)[C@@H](O)[C@H](OCc2ccccc2)[C@H]1OCc1ccccc1] | 85%/24 h | 94%/14 h |
| 5 | 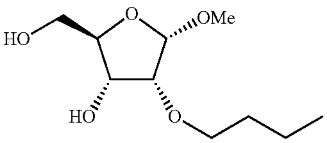 | 77%/24 h | 83%/9 h |

DMN-AZADO was clearly more advantageous in terms of the yield of the target product and the reaction time also in the one-pot oxidation reaction of primary alcohol into carboxylic acid.

EXAMPLE 7-1

Oxidation of 2,2-Dimethyl-5-phenylpentane-1,3-diol

{Chem. 27}

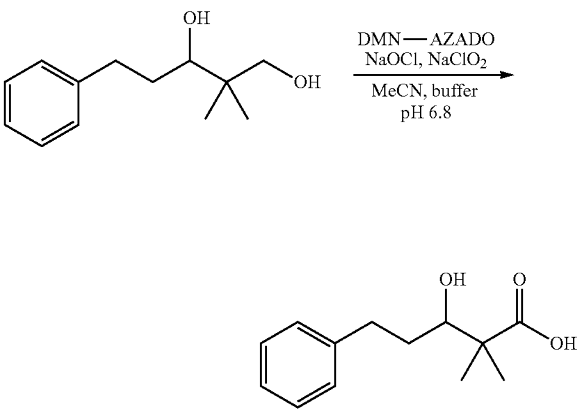

A sodium chlorite aqueous solution (81.0 mg, 0.717 mmol in $H_2O$ (0.4 ml)), and a sodium hypochlorite aqueous solution (0.0146 M, 0.16 ml) were separately and slowly dropped onto an acetonitrile (1.2 ml)-pH 6.8 phosphate buffer (1 M, 0.8 ml) of 2,2-dimethyl-5-phenylpentane-1,3-diol (49.7 mg, 0.239 mmol) and DMN-AZADO (3.97 mg, 0.024 mmol) at room temperature. The mixture was stirred at 25° C. for 1 h, and a pH 2.3 phosphate buffer was added until the mixture was brought to pH 4 or less. The aqueous layer was then saturated with a common salt, and extracted with dichloromethane. The organic layer was dried over sodium sulfate, and the solvent was evaporated under reduced pressure. The resulting residue was dissolved in a diethyl ether solution, and treated with an excess amount of a diazomethane diethyl ether solution to produce a methyl ester product. After evaporating the solvent under reduced pressure, the product was purified by silica gel column chromatography to give a hydroxy ester compound (51.0 mg, 90%).

Methyl 3-Hydroxy-2,2-dimethyl-5-phenylpentanate: $^1$H-NMR (400 MHz, $CDCl_3$) δ 7.38-7.15 (m, 5H), 3.69 (s, 3H), 3.62 (ddd, J=10.4 Hz, 7.0 Hz, 1.7 Hz, 1H), 2.95 (ddd, J=14.7 Hz, 9.8 Hz, 4.9 Hz, 1H), 2.65 (ddd, J=13.6 Hz, 9.2 Hz, 6.8 Hz, 1H), 2.57 (d, J=7.0 Hz, 1H), 1.87-1.70 (m, 1H), 1.70-1.50 (m, 1H), 1.19 (s, 3H), 1.16 (s, 3H); $^{13}$C-NMR (100 MHz, $CDCl_3$) δ 178.1, 142.0, 128.4, 128.3, 125.8, 76.0, 51.8, 47.1, 33.6, 32.8, 22.3, 20.3; IR (neat, $cm^{-1}$): 3501, 2951, 1723, 1455, 1275, 1134, 1075, 701; MS m/z 236 ($M^+$), 117 (100%); HRMS (EI) calcd for $C_{14}H_{20}O_3$ 236.1413 ($M^+$), found 236.1401.

EXAMPLE 7-2

Oxidation of Isopropyl 2,3-Deoxy-α-D-glucopyranoside

{Chem. 28}

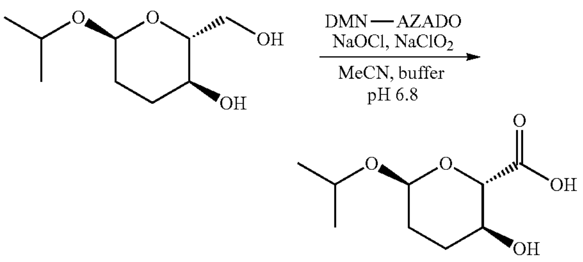

Isopropyl 2,3-deoxy-α-D-glucopyranoside (50.0 mg, 0.263 mmol) was oxidized in the same manner as in Example 7-1 to give the desired methyl ester compound (55.6 mg, 97%).

Methyl(isopropyl-2,3-deoxy-α-D-glucopyranoside)uronate: $^1$H-NMR (400 MHz, $CDCl_3$) δ 5.01 (t, J=2.4 Hz, 1H), 4.19 (d, J=9.2 Hz, 1H), 3.95 (sept, J=6.3H, 1H), 3.83 (s, 3H), 3.84-3.74 (d m, J=2.4 Hz, 1H), 3.15 (s, 1H), 1.98-1.81 (m, 2H), 1.81-1.72 (m, 2H), 1.23 (d, J=6.3 Hz, 3H), 1.15 (d, J=6.3 Hz, 3H); $^{13}$C-NMR (100 MHz, $CDCl_3$) δ 172.3, 94.3, 72.2, 68.7, 67.4, 52.4, 28.9, 25.8, 23.2, 21.3; IR (neat, $cm^{-1}$): MS m/z 175 ($M^+$-$C_3H_7$), 129 (100%); HRMS (EI) calcd for $C_7H_{11}O_5$ 175.0607 ($M^+$-$C_3H_7$), found 175.0607.

EXAMPLE 7-3

Oxidation of 2,2,4-Trimethylpentane-1,3-diol

{Chem. 29}

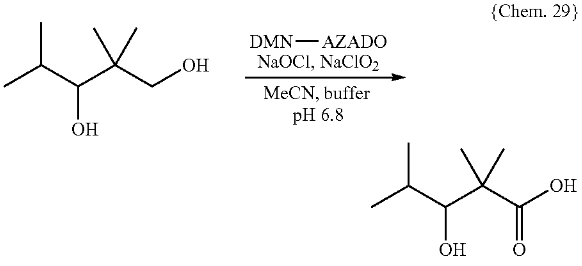

2,2,4-Trimethylpentane-1,3-diol (44.4 mg, 0.304 mmol) was oxidized in the same manner as in Example 7-1 to give the desired methyl ester compound (48.7 mg, 92%).

Methyl 3-Hydroxy-2,2,4-trimethylpentanate: $^1$H-NMR (400 MHz, $CDCl_3$) δ 3.69 (s, 3H), 3.39 (dd, J=8.7 Hz, 3.6 Hz, 1H), 2.81 (d, J=8.7 Hz, 1H), 1.86 (sept d, J=6.9 Hz, 3.6 Hz, 1H), 1.28 (s, 3H), 1.19 (s, 3H), 0.97 (d, J=6.9 Hz, 3H), 0.81 (d, J=6.9 Hz, 3H); $^{13}$C-NMR (100 MHz, $CDCl_3$) δ 178.3, 81.2, 51.6, 45.8, 29.8, 23.0, 22.3, 21.3, 16.2; IR (neat, $cm^{-1}$): 3506, 2961, 2878, 1729, 1472, 1264, 1143, 1030, 994; MS m/z 143 ($M^+$-$CH_3O$), 102 (100%); HRMS (EI) calcd for $C_8H_{15}O_2$ 143.1072 ($M^+$-$CH_3O$), found 143.1063.

EXAMPLE 7-4

Oxidation of Methyl 2,3-bis-O-(Phenylmethyl)-β-D-glucopyranoside

{Chem. 30}

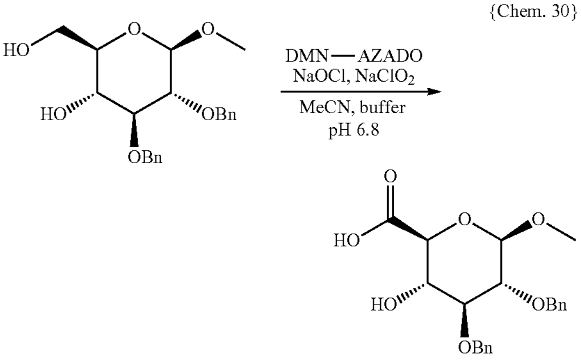

Methyl 2,3-bis-O-(phenylmethyl)-β-D-glucopyranoside (41.8 mg, 0.112 mmol) was oxidized in the same manner as in Example 7-1 to give the desired methyl ester compound (42.3 mg, 94%).

Methyl (methyl-2,3-bis-O-(phenylmethyl)-β-D-glucopyranoside)uronate: $^1$H-NMR (400 MHz, $CDCl_3$) δ 7.38-7.25 (m, 10H), 4.90 (d, J=11.2 Hz, 1H), 4.89 (d, J=11.2 Hz, 1H), 4.80 (d, J=11.2 Hz, 1H), 4.71 (d, J=11.2 Hz, 1H), 4.37 (d, J=8.3 Hz, 1H), 3.87-3.81 (m, 2H), 3.83 (s, 3H), 3.59 (s, 3H), 3.52 (dd, J=8.3 Hz, 8.3 Hz, 1H), 3.44 (dd, J=8.3 Hz, 8.3 Hz, 1H), 2.80 (s, 1H); $^{13}$C-NMR (100 MHz, $CDCl_3$) δ 169.7, 138.4, 138.3, 128.4, 128.3, 128.0, 127.9, 127.8, 127.7, 105.0, 83.0, 81.1, 75.3, 74.8, 74.2, 71.7, 57.4, 52.7; IR (neat, $cm^{-1}$): 3490, 2909, 1749, 1454, 1210, 1069, 738, 698; MS m/z 402 ($M^+$), 311 (100%); HRMS (EI) calcd for $C_{22}H_{26}O_7$ 402.1679 ($M^+$), found 402.1642.

EXAMPLE 7-5

Oxidation of Methyl 2-O-n-Butyl-α-D-ribofuranoside

{Chem. 31}

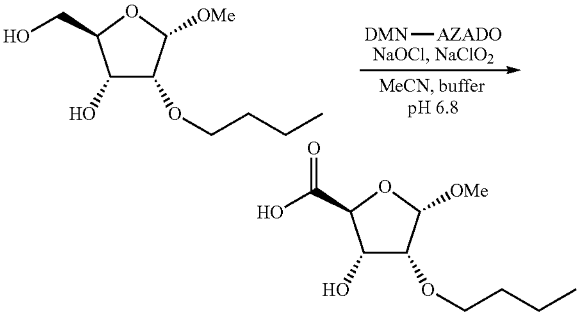

Methyl 2-O-n-butyl-α-D-ribofuranoside (41.5 mg, 0.188 mmol) was oxidized in the same manner as in Example 7-1 to give the desired methyl ester compound (38.8 mg, 83%).

Methyl(methyl-2-O-n-butyl-α-D-ribofuranoside)uronate: $^1$H-NMR (400 MHz, $CDCl_3$) δ 5.11 (d, J=4.4 Hz, 1H), 4.65

(d, J=2.0 Hz, 1H), 4.29 (ddd, J=8.8 Hz, 5.9 Hz, 2.0 Hz, 1H), 3.86 (dd, J=5.9 Hz, 4.4 Hz, 1H), 3.79 (s, 3H), 3.63 (dt, J=9.3 Hz, 6.8 Hz, 1H), 3.56 (dt, J=9.3 Hz, 6.8 Hz, 1H), 3.48 (s, 3H), 3.21 (d, J=8.8 Hz, 1H), 1.65 (dt, J=6.8 Hz, 6.8 Hz, 1H), 1.63 (dt, J=6.8 Hz, 6.8 Hz, 1H), 1.39 (dq, J=14.6 Hz, 7.3 Hz, 2H), 0.93 (t, J=7.3 Hz, 3H); $^{13}$C-NMR (100 MHz, $CDCl_3$) δ 170.7, 102.6, 83.7, 78.2, 71.8, 70.6, 55.5, 52.4, 31.6, 19.0, 13.7; IR (neat, $cm^{-2}$): 3528, 2957, 1753, 1439, 1208, 1090, 1055; MS m/z 247 ($M^+$-H), 159 (100%); HRMS (EI) calcd for $C_{11}H_{19}O_6$ 247.1182 ($M^+$-H), found 247.1179.

EXAMPLE 8

TEMPO and DMN-AZADO were compared for catalytic activity in the oxidation reaction of a diol into a medium-membered lactone using diacetoxyiodobenzene.

TABLE 7

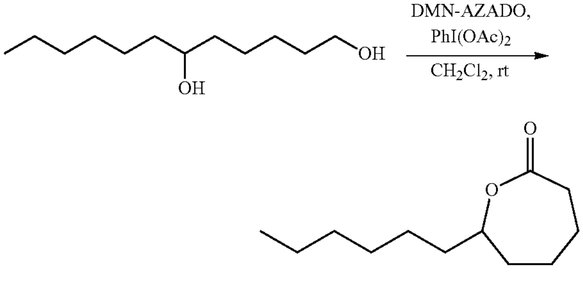

| entry | catalyst | loading amount (mol %) | time | yield |
|---|---|---|---|---|
| 1 | TEMPO | 10 | 8.5 h | 82% |
| 2 | | 5 | 9 h | 75% |
| 3 | DMN-AZADO | 10 | 2 h | 83% |
| 4 | | 5 | 3 h | 78% |

DMN-AZADO was shown to advantageously afford a shorter reaction time than TEMPO.

EXAMPLE 8-1

Oxidation of Dodecane-1,6-diol

{Chem. 32}

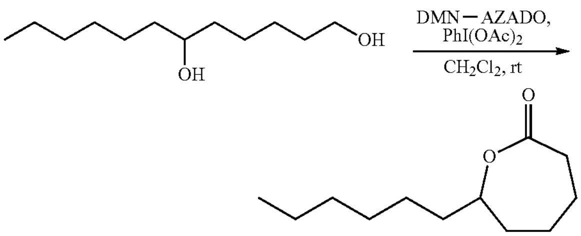

DMN-AZADO (3.69 mg, 0.0222 mmol) and diacetoxyiodobenzene (179 mg, 0.555 mmol) were added to a dichloromethane solution (2.2 ml) of dodecane-1,6-diol (44.9 mg, 0.222 mmol), and the mixture was stirred at room temperature for 2 h. This was followed by addition of saturated sodium bicarbonate water and a saturated sodium thiosulfate solution, and extraction with dichloromethane. The organic layer was washed with saturated brine, and dried over magnesium sulfate. The solvent was evaporated under reduced pressure. The residue was then purified by silica gel column chromatography to give a lactone product (36.5 mg, 83%).

6-Hexyl-ε-caprolactone: $^{1}$H-NMR (400 MHz, $CDCl_3$) δ 4.23 (ddt, J=7.8 Hz, 3.9 Hz, 3.9 Hz, 1H), 2.78-2.48 (m, 2H), 2.06-1.81 (m, 3H), 1.81-1.40 (m, 6H), 1.40-1.18 (m, 7H), 0.88 (t, J=6.4 Hz, 3H); $^{1}$C-NMR (100 MHz, $CDCl_3$) δ 175.8, 80.5, 36.3, 34.9, 34.5, 31.6, 29.0, 28.2, 25.3, 23.0, 22.5, 14.0; IR (neat, $cm^{-1}$): 2931, 2859, 1730, 1448, 1175, 1013; MS m/z 199 ($M^+$+H), 85 (100%); HRMS (EI) calcd for $C_{12}H_{23}O_2$ 199.1698 ($M^+$+H), found 199.1688.

TABLE 8

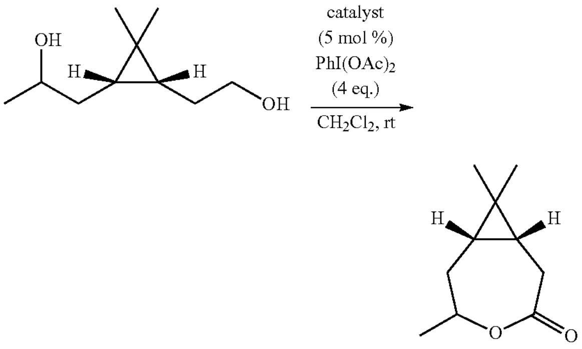

| catalyst | yield/time |
|---|---|
| TEMPO | 77%/18 h |
| DMN-AZADO | 75%/2 h |

DMN-AZADO was shown to advantageously afford a shorter reaction time than TEMPO even with a different substrate.

EXAMPLE 8-2

Oxidation of (1R,3S)-2,2-Dimethyl-3-(2-hydroxypropyl)-1-(2-hydroxyethyl)cyclopropane {Chem. 33}

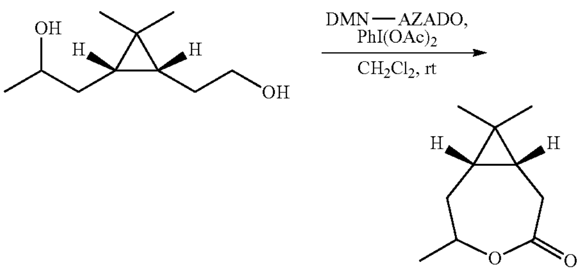

(1R,3S)-2,2-Dimethyl-3-(2-hydroxypropyl)-1-(2-hydroxyethyl)cyclopropane (44.5 mg, 0.258 mmol) was oxidized in the same manner as in Example 8-1 to give the desired compound (32.7 mg, 75%).

(1R,7S)-5,8,8-Trimethyl-4-oxabicyclo[5.1.0]octan-3-one: $^{1}$H-NMR (400 MHz, $CDCl_3$) δ 4.68-4.58 (m, 0.5H), 4.14 (dqd, J=12.0 Hz, 6.0 Hz, 3.0 Hz, 0.5H), 3.17 (dd, J=15.5 Hz, 4.8 Hz, 0.5H), 2.97 (dd, J=15.5 Hz, 4.1 Hz, 0.5H), 2.77 (dd, J=14.5 Hz, 8.0 Hz, 0.5H), 2.42 (dd, J=14.5 Hz, 10.1 Hz, 0.5H), 2.20-2.02 (m, 1H), 1.87 (dd, J=15.5 Hz, 1.9 Hz, 0.5H), 1.80 (ddd, J=15.9 Hz, 10.6 Hz, 5.3 Hz, 0.5H), 1.32 (d, J=6.0 Hz, 1.5H), 1.31 (d, J=6.0 Hz, 1.5H), 1.074 (s, 1.5H), 1.067 (s, 1H), 1.05 (s, 1.5H), 1.04 (s, 1.5H), 1.03-0.85 (m, 1H), 0.78-0.65 (m, 1H); $^{13}$C-NMR (100 MHz, $CDCl_3$) δ 173.8, 173.1, 76.9, 73.9, 33.0, 30.7, 30.6, 29.1, 29.0, 28.5, 22.1, 22.0, 21.7, 20.7, 19.9, 19.8, 18.7, 18.0, 14.8, 14.7; IR (neat, $cm^{-1}$): 2980, 2938, 2868, 1734, 1277, 1193, 1069, 1057; MS m/z 168 ($M^+$), 81 (100%); HRMS (EI) calcd for $C_{10}H_{16}O_2$ 168.1150 ($M^+$), found 168.1143.

EXAMPLE 9

TEMPO and DMN-AZADO were compared for catalytic activity in an oxidation reaction from a diol, using 2,2-dimethyl-5-phenylpentane-1,3-diol.

TABLE 9

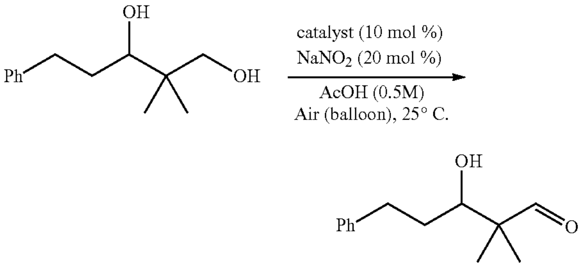

| entry | catalyst | time | yield |
|---|---|---|---|
| 1 | TEMPO | 24 h | 72% |
| 2 | DMN-AZADO | 18 h | 90% |

DMN-AZADO was shown to advantageously afford a shorter reaction time than TEMPO.

EXAMPLE 9-1

Oxidation of 2,2-Dimethyl-5-phenylpentane-1,3-diol

{Chem. 34}

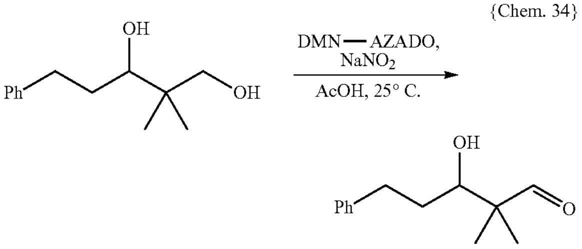

DMN-AZADO (3.16 mg, 19 μmol) and sodium nitrite (2.62 mg, 38 μmol) were added to an acetic acid solution (380 μl) of 2,2-dimethyl-5-phenylpentane-1,3-diol (39.6 mg, 0.190 mmol), and the mixture was stirred at room temperature (25° C.) under atmospheric pressure for 18 h. The mixture was diluted with diethyl ether, and rapidly cooled with saturated sodium bicarbonate and 20% sodium thiosulfate. The solution was then extracted with diethyl ether. The organic layer was dried over sodium sulfate, and concentrated under reduced pressure. The residue was then purified by silica gel column chromatography to give hydroxyaldehyde (35.4 mg, 90%).

3-Hydroxy-2,2-dimethyl-5-phenylpentanal: $^1$H-NMR (400 MHz, $CDCl_3$) δ 9.51 (s, 1H), 7.36-7.17 (m, 5H), 3.77 (d, J=9.7 Hz, 1H), 2.96 (ddd, J=14.0 Hz, 9.7 Hz, 5.4 Hz, 1H), 2.67 (ddd, J=14.0 Hz, 9.2 Hz, 7.3 Hz, 1H), 2.29 (br s, 1H), 1.83-1.64 (m, 2H), 1.11 (s, 3H), 1.04 (s, 3H); $^{13}$C-NMR (100 MHz, $CDCl_3$) δ 206.6, 141.6, 128.3, 125.8, 74.0, 50.3, 33.0, 32.5, 18.8, 16.3; IR (neat, $cm^{-1}$): 3466, 2959, 2871, 1721, 1455, 1075, 1046, 700; MS m/z 188 ($M^+$-$H_2O$), 72 (100%); HRMS (EI) calcd for $C_{13}H_{16}O$ 188.1201 ($M^+$-$H_2O$), found 188.1189.

INDUSTRIAL APPLICABILITY

The present invention provides an oxidation catalyst that is more active than the existing oxidation catalyst TEMPO, and is more selective than AZADO and 1-Me-AZADO in the selective oxidation reaction of primary alcohol.

The DMN-AZADO according to the present invention is applicable to primary alcohol selective oxidation reactions, contributing to simplifying the syntheses of high value-added organic compounds such as pharmaceuticals, pharmaceutical raw materials, agricultural chemicals, cosmetics, and organic materials.

The invention claimed is:

1. A 9-azanoradamantane N-oxyl compound represented by the following formula (1):

{Chem. 1}

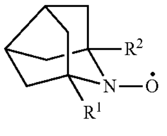

(1)

wherein $R^1$ and $R^2$ represent hydrogen atoms or alkyl groups, and when one of $R^1$ and $R^2$ is hydrogen, the other is an alkyl group.

2. An organic oxidation catalyst that comprises the 9-azanoradamantane N-oxyl compound of claim 1.

3. The catalyst of claim 2, wherein the catalyst has primary alcohol selectivity.

4. A method for producing a 9-azanoradamantane N-oxyl compound represented by the formula (1), the method producing the 9-azanoradamantane N-oxyl compound through at least a step of oxidizing an azanoradamantane compound represented by the following formula (2):

{Chem. 2}

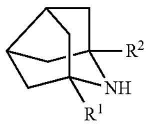

(2)

wherein $R^1$ and $R^2$ have the same definitions as described above.

5. A method for producing a 9-azanoradamantane N-oxyl compound represented by the formula (1), the method producing the 9-azanoradamantane N-oxyl compound through at least a step of closing the ring of a hydrazonoazabicyclo[3.3.1]nonane compound of the formula (3) below and forming an azanoradamantane ring, and oxidizing the resulting azanoradamantane compound represented by the formula (2):

{Chem. 3}

(3)

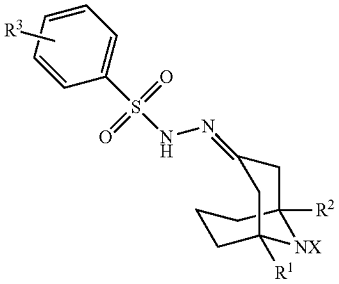

wherein $R^1$ and $R^2$ have the same definitions as described above; $R^3$ represents at least one substituent selected from the group consisting of a hydrogen atom, a halogen atom, a nitro group, a cyano group, a hydroxyl group, a mercapto group, an amino group, a formyl group, a carboxyl group, a sulfo group, a linear or branched $C_{1-12}$ alkyl group, a $C_{3-12}$ cycloalkyl group, a ($C_{1-12}$ alkyl)oxy group, a ($C_{3-12}$ eyeloalkyl)oxy group, a ($C_{1-12}$ alkyl) thio group, a ($C_{3-12}$ cycloalkyl)thio group, a ($C_{1-12}$ alkyl)amino group, a ($C_{3-12}$ cycloalkyl)amino group, a di($C_{1-6}$ alkyl)amino group, a di($C_{3-6}$ cycloalkyl) amino group, a $C_{1-12}$ alkylearbonyl group, a $C_{3-12}$ cycloalkylcarbonyl group, a ($C_{1-12}$ alkyl)oxycarbonyl group, a ($C_{3-12}$ cycloalkyl)oxycarbonyl group, a ($C_{1-12}$ alkyl)thiocarbonyl group, a ($C_{3-12}$ cycloalkyl)thiocarbonyl group, a ($C_{1-12}$ alkyl) aminocarbonyl group, a ($C_{3-12}$ cycloalkyl)aminocarbonyl group, a di($C_{1-6}$ alkyl)aminocarbonyl group, a di($C_{3-6}$ cycloalkyl)aminocarbonyl group, a ($C_{1-12}$ alkyl)carbonyloxy group, a ($C_{3-12}$ cycloalkyl)carbonyloxy group, a ($C_{1-12}$ alkyl) carbonylthio group, a ($C_{3-12}$ cycloalkyl)carbonylthio group, a ($C_{1-12}$ alkyl)carbonylamino group, a ($C_{3-12}$ cycloalkyl)carbonylamino group, a di($C_{1-12}$ alkylcarbonyl)amino group, a di($C_{3-12}$ cycloalkylcarbonyl)amino group, a $C_{1-6}$ haloalkyl group, a $C_{3-6}$ halocycloalkyl group, a $C_{2-6}$ alkenyl group, a $C_{3-6}$ cycloalkenyl group, a $C_{2-6}$ haloalkenyl group, a $C_{3-6}$ halocycloalkenyl group, a $C_{2-6}$ alkynyl group, a $C_{2-6}$ haloalkynyl group, a benzyl group which may be optionally substituted with Ra, a benzyloxy group which may be optionally substituted with Ra, a benzylthio group which may be optionally substituted with Ra, a benzylamino group which may be optionally substituted with Ra, a dibenzylamino group which may be optionally substituted with Ra, a benzylcarbonyl group which may be optionally substituted with Ra, a benzyloxycarbonyl group which may be optionally substituted with Ra, a benzylthiocarbonyl group which may be optionally substituted with Ra, a benzylaminocarbonyl group which may be optionally substituted with Ra, a dibenzylaminocarbonyl group which may be optionally substituted with Ra, a benzylcarbonyloxy group which may be optionally substituted with Ra, a benzylcarbonylthio group which may be optionally substituted with Ra, a benzylcarbonylamino group which may be optionally substituted with Ra, a di(benzylcarbonyl)amino group which may be optionally substituted with Ra, an arylamino group which may be optionally substituted with Ra, an aryloxy group which may be optionally substituted with Ra, an arylthio group which may be optionally substituted with Ra, an arylamino group which may be optionally substituted with Ra, a diarylamino group which may be optionally substituted with Ra, an arylcarbonyl group which may be optionally substituted with Ra, an aryloxycarbonyl group which may be optionally substituted with Ra, an arylthiocarbonyl group which may be optionally substituted with Ra, an arylaminocarbonyl group which may be optionally substituted with Ra, a diarylaminocarbonyl group which may be optionally substituted with Ra, an arylcarbonyloxy group which may be optionally substituted with Ra, an arylcarbonylthio group which may be optionally substituted with Ra, an arylcarbonylamino group which may be optionally substituted with Ra, and a di(arylcarbonyl)amino group which may be optionally substituted with Ra, wherein the substituents may be the same or different when two or more substituents exist; Ra represents halogen, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkyl sulfenyl $C_{1-6}$ alkyl group, a $C_{1-6}$ haloalkoxy group, a $C_{1-6}$ alkyl sulfenyl group, a $C_{1-6}$ alkylsulfinyl group, a $C_{1-6}$ alkylsulfonyl group, a $C_{1-6}$ haloalkylsulfenyl group, a $C_{1-6}$ haloalkylsulfenyl group, a $C_{1-6}$ haloalkylsulfonyl group, a $C_{2-6}$ alkenyl group, a $C_{2-6}$ haloalkenyl group, a $C_{2-6}$ alkenyloxy group, a $C_{2-6}$ haloalkenyloxy group, a $C_{2-6}$ alkenylsulfenyl group, a $C_{2-6}$ alkenylsulfinyl group, a $C_{2-6}$ alkenylsulfonyl group, a $C_{2-6}$ haloalkenylsulfenyl group, a $C_{2-6}$ haloalkenylsulfinyl group, a $C_{2-6}$ haloalkenylsulfonyl group, a $C_{2-6}$ alkynyl group, a $C_{2-6}$ haloalkynyl group, a $C_{2-6}$ alkynyloxy group, a $C_{2-6}$ haloalkynyloxy group, a $C_{2-6}$ alkynyl sulfenyl group, a $C_{2-6}$ alkynylsulfinyl group, a $C_{2-6}$ alkynylsulfonyl group, a $C_{2-6}$ haloalkynyl sulfenyl group, a $C_{2-6}$ haloalkynylsulfinyl group, a $C_{2-6}$ haloalkynylsulfonyl group, —$NO_2$, —CN, a formyl group, —OH, —SH, —$NH_2$, —SCN, a $C_{1-6}$ alkoxycarbonyl group, a $C_{1-6}$ alkylcarbonyl group, a $C_{1-6}$ haloalkylcarbonyl group, a $C_{1-6}$ alkylcarbonyloxy group, a phenyl group, a $C_{1-6}$ alkylamino group, or a di $C_{1-6}$ alkylamino group, wherein Ra is substituted in numbers of 1 to 5, and may be the same or different when two or more Ra exist; and X represents a hydrogen atom, or a group selected from an acyl group, a carbamoyl group, a sulfoneamide group, an alkyl group, an allyl group, a benzyl group, an aryl group, a silyl group, a hydroxyl group, an alkoxy group, and an oxygen atom.

6. A method for producing a 9-azanoradamantane N-oxyl compound represented by the formula (1), the method producing the 9-azanoradamantane N-oxyl compound through at least a step of condensing a keto-azabicyclo[3.3.1 ]nonane compound of the formula (4) below with phenylhydrazine, closing the ring of the resulting hydrazonoazabicyclo[3.3.1]nonane of the formula (3) and forming an azanoradamantane ring, and oxidizing the resulting azanoradamantane compound represented by the formula (2):

{Chem. 4}

(4)

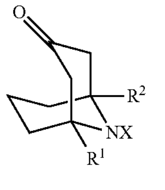

wherein $R^1$, $R^2$, and X have the same definitions as described above.

7. A method for producing a azanoradamantane N-oxyl compound represented by the formula (1), the method comprising:

synthesizing a ketobicycloamine product through condensation of 2,6-heptanedione, ammonium chloride, and acetonedicarboxylic acid, the 2,6-heptanedione being obtained by methylating a Weinreb diamide produced from glutaryl chloride;

producing a hydrazone through condensation of the ketobicycloamine product with hydrazine;

forming an azanoradamantane skeleton under basic condition; and oxidizing the amino group.

8. A method for oxidizing a primary alcohol and/or a secondary alcohol, the method comprising oxidizing the alcohol in the presence of the 9-azanoradamantane N-oxyl compound of claim 1 to synthesize a corresponding oxo product.

9. The method according to claim 8, wherein the oxidation is performed in the presence of a co-oxidizing agent.

10. The method according to claim 8, wherein the alcohol is a compound that includes a primary alcohol and a secondary alcohol, and wherein the method selectively oxidizes the primary alcohol.

11. The method according to claim 8, wherein the 9-azanoradamantane N-oxyl compound is added in 0.001 mol % to 1000 mol % with respect to the alcohol.

12. The method according to claim 9, wherein the co-oxidizing agent is an oxidizing agent selected from the group consisting of peroxy acid, hydrogen peroxide, hypohalous acid and salts thereof, perhalic acid and salts thereof, persulfates, halides, halogenating agents, trihaloisocyanuric acids, (diacetoxyiodo)arenes, oxygen, and air.

13. The method according to claim 9, wherein the 9-azanoradamantane N-oxyl compound is added in 0.001 mol % to 1000 mol % with respect to the alcohol.

14. The method according to claim 10, wherein the 9-azanoradamantane N-oxyl compound is added in 0.001 mol % to 1000 mol % with respect to the alcohol.

15. The method according to claim 10, wherein the co-oxidizing agent is an oxidizing agent selected from the group consisting of peroxy acid, hydrogen peroxide, hypohalous acid and salts thereof, perhalic acid and salts thereof, persulfates, halides, halogenating agents, trihaloisocyanuric acids, (diacetoxyiodo)arenes, oxygen, and air.

16. The method according to claim 11, wherein the co-oxidizing agent is an oxidizing agent selected from the group consisting of peroxy acid, hydrogen peroxide, hypohalous acid and salts thereof, perhalic acid and salts thereof, persulfates, halides, halogenating agents, trihaloisocyanuric acids, (diacetoxyiodo)arenes, oxygen, and air.

* * * * *